(12) United States Patent
Van Der Zaag et al.

(10) Patent No.: US 10,373,705 B2
(45) Date of Patent: Aug. 6, 2019

(54) PROVIDING NUCLEOTIDE SEQUENCE DATA

(75) Inventors: Pieter Jan Van Der Zaag, Waalre (NL); Ronny Amberg, Berlin (DE); Peter Beyerlein, Wildau (DE); Wilhelmus Franciscus Johannes Verhaegh, Heusden Gem. Asten (NL); Rene Boettcher, Berlin (DE)

(73) Assignee: Koninklijke Philips N.V., Eindhoven (NL)

( * ) Notice: Subject to any disclaimer, the term of this patent is extended or adjusted under 35 U.S.C. 154(b) by 208 days.

(21) Appl. No.: 14/124,380

(22) PCT Filed: Apr. 17, 2012

(86) PCT No.: PCT/IB2012/051920
§ 371 (c)(1),
(2), (4) Date: Dec. 6, 2013

(87) PCT Pub. No.: WO2012/168803
PCT Pub. Date: Dec. 13, 2012

(65) Prior Publication Data
US 2014/0329690 A1   Nov. 6, 2014

(30) Foreign Application Priority Data

Jun. 7, 2011 (EP) .................................. 11168968
Dec. 22, 2011 (EP) .................................. 11195103

(51) Int. Cl.
*G16B 30/00* (2019.01)
*C12Q 1/6874* (2018.01)
*G16B 25/00* (2019.01)

(52) U.S. Cl.
CPC ........... *G16B 30/00* (2019.02); *C12Q 1/6874* (2013.01); *G16B 25/00* (2019.02)

(58) Field of Classification Search
None
See application file for complete search history.

(56) References Cited

U.S. PATENT DOCUMENTS

| | | | |
|---|---|---|---|
| 7,244,559 | B2 | 7/2007 | Rothberg et al. |
| 8,507,456 | B2 | 8/2013 | Purschke et al. |
| 9,110,075 | B2 | 8/2015 | Singh et al. |
| 2001/0051714 | A1 | 12/2001 | Chen et al. |
| 2003/0231986 | A1 | 12/2003 | Kocher |
| 2005/0147976 | A1 | 7/2005 | Su |
| 2009/0202984 | A1 | 8/2009 | Cantor |
| 2010/0184159 | A1 | 7/2010 | Vissarion et al. |
| 2011/0311975 | A1 | 12/2011 | DeStolpe et al. |
| 2013/0210008 | A1 | 8/2013 | Feitsma et al. |

FOREIGN PATENT DOCUMENTS

| | | |
|---|---|---|
| CN | 101333564 A | 12/2008 |
| JP | 2003515149 A | 4/2003 |
| WO | 2002096552 A2 | 12/2002 |
| WO | 2010097775 A1 | 9/2010 |

OTHER PUBLICATIONS

Li et al. Bioinformatics, v 25, No. 14, pp. 1754-1760, 2009.*
Chou et al Clinical Chemisty 56:1, 62-72 (2010).*
Bentley, D. R. et al., "Accurate whole human genome sequencing using reversible terminator chemistry". 2008 Nature, 456, 53-59.
Johansson, H. et al. "Targeted resequencing of candidate genes using selector probes". Nucleic Acids Research, 2011, vol. 39, No. 2, e8, pp. 1-13.
Hubscher, U. et al., "DNA Polymerases: Discovery, Characterization and Functions in Cellular DNA Transactions", 2010, 1st ed, World Scientific Publishing Co.
McNeil L.K. et al, "The National Microbial Pathogen Database Resource (NMPDR): a genomics platform based on subsystem annotation", Nucleic Acids Res., 2007; 35 (Database Issue): D347-53.
Beishaw, R et al, The RNA Virus Database, Nucleic Acids Res., 2009; 37 (Database issue): D431-435.
Ng, S.B. et al. "Targeted capture and massively parallel sequencing of 12 human exomes". Nature, Sep. 10, 2009, 461(7261) 272.6.
Dean F. B. et al. "Rapid amplification of plasmid and phage DNA using Phi 29 DNA polymerase and multiply-primed rolling circle amplification". Genome Reserach, Woodbury, NY vol. 11, No. 6, Jun. 1, 2001, pp. 1095-1099.
Braeckmans K. et al: "Encoding microcarriers: present and future technologies". Nature Reviews. Drug Discovery, Nature Publishing Group, GB. vol. 1, No. 6, Jun. 1, 2002, pp. 447-456.
Hodges, E. et al. "Genome-wide in situ exon capture for selective resequencing". Nature Genetics 39, 1522-1527 (2007).
Albert, T.J. et al. "Direct selection of human genomic loci by microarray hybridization". Nature Methods—4, 903-905 (2007).
Dahl, F. et al. "Multiplex amplification enabled by selective circularization of large sets of genomic DNA fragments". Nucleic Acids Research, 2005, vol. 33, No. 8.

* cited by examiner

Primary Examiner — Joseph Woitach

(57) ABSTRACT

A sequencer device generates basic nucleotide sequence data 30 comprising probe data 34 of a capture probe in the sequencer device 10 and a determined sequence of identifiers 32 of a fragment of nucleic acids captured by the probe. The sequencer device outputs enriched nucleotide sequence data 36 that is enriched with data comprising a reference to a sequence 38 that is expected for the fragment of nucleic acids.

13 Claims, 17 Drawing Sheets
Specification includes a Sequence Listing.

| 3,1Gb | 32,6Mb | 32,6Mb | 3,2Mb | 3,2Mb | ~30mio | ~3mio | ~300k |
|---|---|---|---|---|---|---|---|
| 9mio | 9mio | 3mio | 9mio | 3mio | 3mio | 3mio | 3mio |
| 59m 23s | 2m 5s | 55s | 1m 19s | 30s | 40s | 31s | 28s |

FIG. 5A

| Aligner / Algorithm | NW | NWBem | Bowtie | BWA | MAQ |
|---|---|---|---|---|---|
| Virtual memory required | 200 | 200 | 1,202 | 2,333 | 2,666 |
| of which is physical memory | 145 | 145 | 904 | 2,322 | 2,654 |

FIG. 5B 60
62    64 66   70  74

@HWUSI-EAS100R:6:73:941:1973#0/1

76   48                                68  70   60
                                                  78
@ENSG00000142168x33031935x33032154x21:1:10:17:18#NNNNNN/1
TGCTGAAGGGCGACGGCCCAGTGCAGGGCATCATCAAT
TTCGAGCAGAAG
+ENSG00000142168x33031935x33032154x21:1:10:17:18#NNNNNN/1
hhhhhhhhhhhhhhhhhhhhhhhhhhhhhhhhhhhhhhhhhhhhhhhh

FIG. 7

48                              68 70
                                         60
>ENSG00000142168|33031935|33032154|21_17|18
76   TGCTGAAGGGCGACGGCCCAGTGCAGGGCAT     78
     CATCAATTTCGAGCAGAAG

FIG. 8

48                              68 70
>ENSG00000142168|33031935|33032154|21_17|15
CGAAGGCCGTGTGCGTGCTGAAGGGCGACG    80
GCCCAGTGCAGGGCATCATC
42  >ENSG00000142168|33031935|33032154|21_17|16
GCCGTGTGCGTGCTGAAGGGCGACGGCCCA    80
GTGCAGGGCATCATCAATTT
>ENSG00000142168|33031935|33032154|21_17|17
GTGCGTGCTGAAGGGCGACGGCCCAGTGCA    80
GGGCATCATCAATTTCGAGC
44  >ENSG00000142168|33031935|33032154|21_17|18
TGCTGAAGGGCGACGGCCCAGTGCAGGGCA    80
TCATCAATTTCGAGCAGAAG

FIG. 9

| 17 | 15 | CGAAGGCCGTGTGCGTGCTGAAGG<br>GCGACGGCCCAGTGCAGGGCATCATC |
|---|---|---|
| 17 | 16 | GCCGTGTGCGTGCTGAAGGGCGAC<br>GGCCCAGTGCAGGGCATCATCAATTT |
| 17 | 17 | GTGCGTGCTGAAGGGCGACGGCCC<br>AGTGCAGGGCATCATCAATTTCGAGC |
| 17 | 18 | TGCTGAAGGGCGACGGCCCAGTGC<br>AGGGCATCATCAATTTCGAGCAGAAG |

FIG. 10

@ENSG00000142168x33031935x33032154x21_171:1:10:17:18
NNNNNN/1
TGCTGAAGGGCGACGGCCCAGTGCAGGGCATCATCAATTT
CGAGCAGAAG
+ENSG00000142168x33031935x33032154x21_:171:10:17:18
NNNNNN/1
hhhhhhhhhhhhhhhhhhhhhhhhhhhhhhhhhhhhhhhhhhhhhhhhhh

FIG. 11

>ENSG00000142168|33031935|33032154|21
GTTTGGGGCCAGAGTGGGCGAGGCGCGGAGGTC
TGGCCTATAAAGTAGTCGCGGAGACGGGGTGCTGGTTT
GCGTCGTAGTCTCCTGCAGCGTCTGGGGTTTCCGTTG
CAGTCCTCGGAACCAGGACCTCGGCGTGGCCTAGCG
AGTTATGGCGACGAAGGCCGTGTGCGTGCTGAAGGGC
GACGGCCCAGTGCAGGGCATCATCAATTTCGAGCAGAAG
>ENSG00000196284|45345505|45345690|6
CCCCCCCCATCGCCCCGTCACACAGCCGAGTCACCTT
TTCCCTTTCTACACTCCACACTCTCAGTCCCCACCCC
GCCCCTTTCCAAGCGTGTCCCGGGCCGCAGCAGCAG
AAACCGCACCATCTCCACCCCCACATTCTCCTCGCGG
GAAGCGCAGCAGTGCCTCCAAGGGTTCTTAAAGCAGAG

FIG. 12

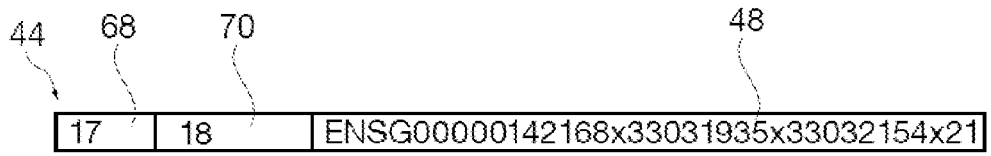
FIG. 13
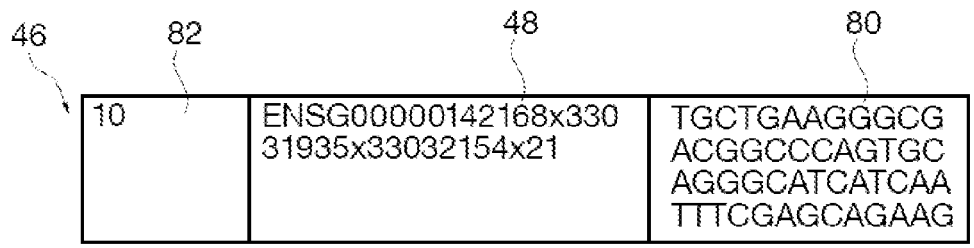
FIG. 14
@TGCTGAAGGGCGACGGCCCAGTGCAGGGCATCATCAA
TTTCGAGCAGAAG:1:10:17:18#NNNNNN/1
76 —— TGCTGAAGGGCGACGGCCCAGTGCAGGGCATCATCAAT
TTCGAGCAGAAG
+TGCTGAAGGGCGACGGCCCAGTGCAGGGCATCATCAA
TTTCGAGCAGAAG:1:10:17:18#NNNNNN/1
hhhhhhhhhhhhhhhhhhhhhhhhhhhhhhhhhhhhhhhhhhhhhhhhhhhh
FIG. 15

```
@ENSG00000142168x33031935x33032154x21_171:1:10:17:18
NNNNNN/1
TGCTGAAGGGCGACGGCCCAGTGCAGGGCATCATCAATTTC
GAGCAGAAG
+ENSG00000142168x33031935x33032154x21_:171:10:17:18
NNNNNN/1
hhhhhhhhhhhhhhhhhhhhhhhhhhhhhhhhhhhhhhhhhhhhhhhhh
```

FIG. 16

```
@ENSG00000142168x33031935x33032154x21_TGCTGAAGGGCG
ACGGCCCAGTGCAGGGCATCATCAATTTCGAGCAGAAG:1:10:17:18
#NNNNNN/1
TGCTGAAGGGCGACGGCCCAGTGCAGGGCATCATCA
ATTTCGAGCAGAAG
+ENSG00000142168x33031935x33032154x21_TGCT
GAAGGGCGACGGCCCAGTGCAGGGCATCATCAATT
TCGAGCAGAAG:10:17:18#NNNNNN/1
hhhhhhhhhhhhhhhhhhhhhhhhhhhhhhhhhhhhhhhhhhhhhhhhh
```

FIG. 17

```
>ENSG00000196284|45345505|45345690|6_51
CTCCACACTCTCAGTCCCCCACCCCGCCCCTTTCCAA
GCGTGTCCCGGGC
```

>ENSG00000196284|45345505|45345690|6_CTCCACACTCTCAG
TCCCCACCCCGCCCCTTTCCAAGCGTGTCCCGGGC
CTCCACACTCTCAGTCCCCCACCCCGCCCCTTTCCAAG   78
CGTGTCCCGGGC

>ENSG00000102468|47471072|47471885|13
AGAAATCATTCACGAGCCCCTCAAAGTCGCACAAAAGAAC
TGCATGGGAAAGTAGGAAGAGCTGTCTGCACCAAGGGAC
TCCTGGTTTCCACGGGAATGGAGTAGCTCTCTGACTGTCT
CGTTCATTTCATCAGACCTCCCTCTATGTGTATGTCATAAGC
TGCAAGGTAGCAACAGCCAGGAGGGCGGACCAAACAGGC
TTTTTCTTCTCCCTCTTTTTGCTACATATTAATATTGGGAAGT
TTTCCTTTGCTTTTGAGAGAAACTGGAGAAATGGCCTTTTG   92
TGCAGATTCCCATTAAGGTAGGTAAGTGGCACTGTGGTAAT
TTTTTAGGCTGAAGGGTGAAGAGAGAACATAAATAAGGCTA
GAAAACAGTATGTCCTCGGAGTGCTGTGAGTGTCYGGCAC
TTCCATCCAAAGCCAACAGTGTTTGTGTCCAGAGTGGAATT
ACTGACATTGGCCACATAGGCTCAGGGTGGCTAGGCACGT
CTGTGGTGATAACTCTGATAAACTATTAGCACTATTTTATTT
AATAGATACACCATTGAACTGGCTTATTTTCTTCAGCAGAAA
TATGCCACCCAGATATTATTCAAAACCTCACATGTGGTAGG
AAATAAGTTGGTTTCGCAGTACCAATTTTTTTCCCCCACCAG
TAATGACAACTTGCCTTACTTGTAAAGAAAGCCCTTTCCCAA
GTAGGTTTCTAAAGGAGGCAGTTCGATCTCTCTCTTTTTGCA
GGCATGAAAATATTTTCCTCAATAGTTGGGTTTTGCTACAGTT
CTATCACCTTCTGTTCTTC

| 82 | 48 | 94 | 92 | 80 |
|---|---|---|---|---|
| 377 | >ENSG000001024 68\|47471072\|4747 1885\|13 | C | ACAGTATGTCCTCGGAGTGCT GTGAGTGTCCGGCACTTCCAT CCAAAGCC | |
| 377 | >ENSG00000102 468\|47471072\|474 71885\|13 | T | ACAGTATGTCCTCGGAGTGCT GTGAGTGTCTGGCACTTCCAT CCAAAGCC | |

```
@ENSG00000102468x47471448x47471497x13_377:1:1:25:14
#NNNNNN/1
ACAGTATGTCCTCGGAGTGCTGTGAGTGTCTGGCACT
TCCATCCAAAGCC
+ENSG00000102468|47471448|47471497|13:1:1:25:14
#NNNNNN/1
hhhhhhhhhhhhhhhhhhhhhhhhhhhhhhhhhhhhhhhhhhhhhhhhh
```

(labels: 48, 94, 82, 68, 70, 60)

FIG. 22

FIG. 26
FIG. 26 A
FIG. 26 B
FIG. 26 C
FIG. 26 D

PROVIDING NUCLEOTIDE SEQUENCE DATA

This application is a national stage application under 35 U.S.C. § 371 of International Application No. PCT/IB2012/051920 filed on Apr. 17, 2012 and published in the English language on Dec. 13, 2012 as International Publication No. WO/2012/168803, which claims priority to European Application No. 11195103.4 filed on Dec. 22, 2011 and European Application No. 11168968.3 filed on Jun. 7, 2011, the entire disclosures of which are incorporated herein by reference.

The Sequence Listing provided in an ASCII text file with (1) "2011P00673WOUS_Sequence_Listing.txt" as the name of the ASCII text file, (2) Jun. 2, 2014 as the date of the creating of the ASCII text file, and (3) 4,217 bytes as the size of the ASCII text file, is herein incorporated by reference.

FIELD OF THE INVENTION

The invention relates to the fields of nucleic acid sequencing and bioinformatics. In particulate, the invention relates to a method for providing nucleotide sequence data, a method for determining a sequence of nucleotides for a nucleic acid sample, a program element, a computer-readable medium and a sequencer device.

BACKGROUND OF THE INVENTION

Recent sequencing techniques allow the simultaneous determination of large quantities of nucleotide sequences. Typically, a DNA or RNA target sample is fragmented by mechanical or enzymatic techniques, after which individual fragments are bound to a substrate (e.g. the wall of a reaction chamber, a microarray or a microcarrier/bead) via a nucleotide linker molecule that is attached to the substrate and that is able to capture a fragment. For technologies other than single molecule sequencing, a PCR-based amplification step follows. Subsequently, nucleotides are stepwise incorporated and identified for each DNA or RNA fragment bound to the substrate. This process is repeated a number of times and the sequencing reads of all the individual fragments are aligned to get the complete sequence of the target sample under investigation.

Currently, targeted resequencing is developing into the standard procedure within the sequencing field, as this may enable one to focus the sequencing on those sections of the DNA that may be clinically relevant. In target sequencing, specific fragments of the target sample are captured by specific capture probes. Although this may be advantageous as it may save sequencing costs, the bioinformatics analysis may be still a very laborious process which takes easily a week for most analyses.

In WO 2010/097775 A1 a capture oligonucleotide probe is attached to an encoded microcarrier, wherein the code of the microcarrier identifies the sequence of the oligonucleotide probe. After the sequence determination, the nucleotide sequence of the capture oligonucleotide probe is identified by determining the code on the microcarrier.

SUMMARY OF THE INVENTION

The speed at which the bioinformatics analysis can be performed may be speeded up, if information on which probes a fragment has been captured is used. Moreover, this may also reduce the alignment errors (and therefore errors in the consensus sequence which is outputted) and thereby may help to meet clinical requirements.

It may be an object of the invention to provide a cheap, fast and/or reliable nucleic acid sequencing method.

This object may be achieved by the subject-matter of the independent claims. Further exemplary embodiments are evident from the dependent claims and the following description.

A first aspect of the invention relates to a method for providing nucleotide sequence data.

According to an embodiment of the invention, the method comprises the steps of: receiving basic nucleotide sequence data comprising a determined sequence of identifiers for nucleotides of a fragment of nucleic acids and probe data of a capture probe that has captured the fragment of nucleic acids; determining an expected sequence of the fragment of nucleic acids by converting the probe data into the expected sequence with information interrelating the probe data and the expected sequence; outputting the nucleotide sequence data comprising the determined sequence of identifiers and a reference to the expected sequence.

In other words, the nucleotide sequence data may be enriched with data comprising a reference to the expected sequence or the expected sequence itself. It has to be understood that the enriched nucleotide sequence data does not necessarily comprise the probe data. Enriched nucleotide sequence data may only comprise the determined sequence and the reference.

For example, the nucleotide sequence data may comprise the basic nucleotide sequence data and a data table interrelating the probe data with the reference to the expected sequence.

A reference to the expected sequence may comprise a genomic position of the expected sequence and/or a reference sequence which may be the first part of the expected sequence. It may also be possible that the reference is the expected sequence itself. In particular, the reference may be or may comprise a genomic identifier (for example an identifier of a gene or an exon) and a start position of the expected sequence in the gene or exon.

It has to be noted that the genomic position may be a position within a specific genome, for example a human reference genome. Due to insertions and deletions, a position on two different genomes may not be identical.

In general, the method is applicable not just to the human genome, but for example also to genomes of other eucaryotes, pathogens or bacteria. Also, the method may be applied to the genome of a cancerous (human) cell.

With the enriched nucleotide sequence data, the alignment process may be considerably speeded up, as a search in a large area (the whole genome) may be replaced by a search in a small area (the target region) in the alignment algorithm. Furthermore, the origin of the sequence regarding forward or reverse reading may have not to be checked, because it may be known which probe has been used and therefore from which strand the sequence originates.

In summary, a sequencing device performing the method may be adapted to generate a nucleotide sequence data before the aligning process, which directly or indirectly codes for the genomic position and/or the expected sequence. The reference to the expected sequence may be added in the sequencing device before, during or after the base calling/sequencing process.

A reference to the expected sequence may also be a software identifier (i.e. a code, for example a numeric value, a software label or a software code) that is adapted to identify an expected sequence. In particular, the genomic position may be encrypted in the software identifier. In such a way, an extra layer of safety may be added for parts of the genome that may be sensitive with respect to the prediction of diseases such as Alzheimer.

The reference to the expected sequence may also be a reference for variants of the expected sequence. Note that the reference to the expected sequence need not be unique. For example, the reference may point to a group of genetic variants of an expected sequence.

According to an embodiment of the invention, the probe data comprises position data and the expected sequence is determined by interrelating the position data with the expected sequence. For example, the position data may be an x-/y-position of the capture probe on a microarray. However, it is also possible that the probe data comprises a label of a microcarrier, for example a bead, to which the capture probe is attached. In a preferred embodiment of the present invention, the probe data comprises position data comprising the x-/y-position of the capture probe on a microcarrier such as a microarray and the expected sequence is determined by interrelating the position data with the expected sequence.

A further aspect of the invention relates to a method for determining the sequence of a target nucleic acid molecule linked to genomic position information of said target nucleic acid molecule comprising the steps of:

providing a capture oligonucleotide probe which comprises two portions which are complementary in sequence to portions of the target nucleic acid, wherein said portions of the capture oligonucleotide probe are separated by a non-target complementary sequence label, and optionally an immobilization moiety;

hybridizing said capture oligonucleotide probe with a sample comprising a nucleic acid molecule, wherein said nucleic acid molecule comprises a sequence which is at least partially complementary to the capture oligonucleotide probe;

optionally immobilizing said capture oligonucleotide probe-target nucleic acid complex on a solid phase;

optionally removing non-bound nucleic acid molecules form the solid phase;

circularizing said nucleic acid target molecule by use of a polymerase activity;

amplifying said circularized nucleic acid target molecule, preferably by rolling circle amplification;

determining the sequence of the amplified nucleic acid target molecules by generating a sequence read of at least 2 nucleotides;

identifying the sequence of the non-target complementary sequence label;

identifying the nucleotide sequence of the capture oligonucleotide probe adjacent to the non-target complementary sequence label, wherein optionally 3' and 5' adjacent sequences are individually identified;

identifying the location of the sequence of the capture oligonucleotide probe on a reference genome; and providing a combination of (i) the determined sequence of the nucleic acid target and (ii) information on its location on a reference genome.

In a preferred embodiment, the present invention relates to a method for providing nucleotide sequence data as defined herein above, wherein said probe data comprises information on the location of the determined sequence of the nucleic acid target on a reference genome obtainable by the method of determining the sequence of a target nucleic acid molecule linked to genomic position information of said target nucleic acid molecule as defined above, and wherein the expected sequence is defined by interrelating the information on said location on a reference genome with the corresponding sequence of the reference genome.

A further aspect of the invention relates to a program element or computer program for providing nucleotide sequence data, which when being executed by a processor is adapted to carry out the steps of the method as described in the above and in the following.

A further aspect of the invention relates to a computer-readable medium, in which such a program element is stored. A computer-readable medium may be a floppy disk, a hard disk, an USB (Universal Serial Bus) storage device, a FLASH memory, a RAM (Random Access Memory) or a ROM (Read Only Memory).

A further aspect of the invention relates to a sequencer device.

According to an embodiment of the invention, the sequencer device is adapted to generate basic nucleotide sequence data comprising a determined sequence of identifiers for nucleotides of a fragment of nucleic acids and probe data of a capture probe that has captured the fragment of nucleic acids; to interrelate the probe data with an expected sequence; and to generate nucleotide sequence data comprising the determined sequence of identifiers and a reference to the expected sequence.

The sequencer device may comprise a processing unit, for example one or more processors, that is adapted to carry out the program element as mentioned above. The sequencer device may comprise or may be connected to a computer-readable medium on which the program element as described is stored.

It has to be understood that features of the method as described in the above and in the following may be features of the computer-readable medium, the program element and the sequencer device as described in the above and in the following and vice versa.

The invention may be applicable in diagnostic DNA and RNA sequencing or in the Life Sciences sequencing market.

BRIEF DESCRIPTION OF THE DRAWINGS

These and other aspects of the invention will be apparent from and elucidated with reference to the embodiments described hereinafter.

In the drawings:

FIG. 5A shows a further diagram indicating the gain in alignment speed according to an embodiment of the invention.

FIG. 5B shows a diagram indicating the RAM requirements (MB) of the different aligners when aligning approximately 5 million reads. Physical memory required is part of the whole virtual memory required by the program. Settings: target size 3 Mb, 20× read redundancy, read length 50 bases, 1% sequencing error, 10% reads off-target.

FIG. 6 shows a header of a read of nucleotide sequence data.

FIG. 7 shows a read of nucleotide sequence data according to an embodiment of the invention, namely SEQ. ID. NO. 1 [tgctgaaggg cgacggccca gtgcagggca tcatcaattt cgagcagaag].

FIG. 8 shows a read of nucleotide sequence data according to an embodiment of the invention, namely SEQ. ID. NO. 1.

FIG. 9 shows a table according to an embodiment of the invention containing SEQ. ID. NO. 2 [cgaaggccgt gtgcgtgctg aagggcgacg gcccagtgca gggcatcatc]; SEQ. ID. NO. 3 [gccgtgtgcg tgctgaaggg cgacggccca gtgcagggca tcatcaattt]; SEQ. ID. NO. 4 [gtgcgtgctg aagggcgacg gcccagtgca gggcatcatc aatttcgagc]; and SEQ. ID NO. 1.

FIG. 10 shows a table according to an embodiment of the invention containing SEQ. ID. NO. 2; SEQ. ID NO. 3; SEQ. ID NO. 4; and SEQ. ID NO. 1.

FIG. 11 shows a read of nucleotide sequence data according to an embodiment of the invention, namely SEQ. ID. NO. 1.

FIG. 12 shows a table according to an embodiment of the invention containing SEQ. ID NO. 5 [gtttgggggcc agagtgggcg aggcgcggag gtctggccta taaagtagtc ctggagacgg ggtgctggtt tgcgtcgtag tctcctgcag cgtctggggt ttccgttgca gtcctcggaa ccaggacctc ggcgtggcct agcgagttat ggcgacgaag gccgtgtgcg tgctgaaggg cgacggccca gtgcagggca tcatcaattt cgagcagaat] and SEQ. ID NO. 6 [ccccccccat cgcccgtca cacagccgag tcaccttttc ccttctaca ctccacactc tcagtccccc accccgcccc ttccaagcg tgtcccggc cgcagcagca gaaccgcac catctccacc cccacattct cctcgcggga agcgcagcag tgcctccaag ggttcttaaa gcagag].

FIG. 13 shows a table according to an embodiment of the invention.

FIG. 14 shows a table according to an embodiment of the invention containing SEQ. ID NO. 1.

FIG. 15 shows a read of nucleotide sequence data according to an embodiment of the invention containing three repetitions of SEQ. ID. NO. 1.

FIG. 16 shows a read of nucleotide sequence data according to an embodiment of the invention, namely SEQ. ID. NO. 1.

FIG. 17 shows a read of nucleotide sequence data according to an embodiment of the invention containing three repetitions of SEQ. ID. NO. 1.

FIG. 18 shows a read of nucleotide sequence data according to an embodiment of the invention, namely SEQ. ID. NO. 7 [ctccacactc tcagtccccc accccgcccc ttccaagcg tgtcccggc].

FIG. 19 shows a read of nucleotide sequence data according to an embodiment of the invention containing two repetitions of SEQ. ID NO. 7.

FIG. 20 shows an example of a variant of a nucleotide sequence, namely SEQ. ID. NO. 8 [agaaatcatt cacgagcccc tcaaagtcgc acaaaagaac tgcatgggaa agtaggaaga gctgtctgca ccaagggact cctggtttcc acgggaatgg agtagctctc tgactgtctc gttcatttca tcagacctcc ctctatgtgt atgtcataag ctgcaaggta gcaacagcca ggagggcgga ccaaacaggc tttttcttct ccctcttttt gctacatatt aatattggga agttttcctt tgcttttgag agaaactgga gaaatggcct tttgtgcaga ttcccattaa ggtaggtaag tggcactgtg gtaattttt aggctgaagg gtgaagagag aacataaata aggctagaaa acagtatgtc ctcggagtgc tgtgagtgtc vggcacttcc atccaaagcc aacagtgttt gtgtccagag tggaattact gacattggcc acataggctc agggtggcta ggcacgtctg tggtgataac tctgataaac tattagcact attttttattt aatagataca ccattgaact ggcttatttt cttcagcaga aatatgccac ccagatatta ttcaaaacct cacatgtggt aggaaataag ttggtttcgc agtaccaatt ttttccccc accagtaatg acaact tgcc ttacttgtaa agaaagccct ttcccaagta ggtttctaaa ggaggcagtt cgatctctct cttttgtcag gcatgaaaat attttcctca atagttgggt tttgcta cag ttctatcacc ttctgttctt c].

FIG. 21 shows a table according to an embodiment of the invention containing SEQ. ID NO. 9 [acagtatgtc ctcggagtgc tgtgagtgtc cggcacttcc atccaaagcc] and SEQ. ID NO. 10 [acagtatgtc ctcggagtgc tgtgagtgtc tggcacttcc atccaaagcc].

FIG. 22 shows a read of nucleotide sequence data according to an embodiment of the invention.

FIG. 25 shows the template which is amplified comprising the head H of the captured target nucleic, the tail T of the captured target nucleic acid fragment, central portion M of the target nucleic acid molecule and section C, which is complementary to the easily identifiable sequence label L.

FIG. 26 shows the potential outcome of a rolling circle amplification and the subsequent processing and sequencing steps necessary to determine the sequence of the target nucleic acid fragment.

FIG. 26 A shows a potential outcome of a rolling circle amplification of a nucleic acid target fragment shown in FIG. 25 with section A' being complementary to section H, section L' being complementary to section C, section B' being complementary to section T and section R being complementary to section M of FIG. 25.

FIG. 26 B shows one option of determining the sequence of the target nucleic acid RCA product, wherein the RCA product is randomly fragmented yielding a fragment comprising a part of R1, a part of R2, A', L' and B'. This fragment can be sequenced with the help of primers P1 and P2. The sequencing may provide reads which overlap, thus completely covering section M or R.

FIG. 26 C shows a further option of determining the sequence of the target nucleic acid RCA product, wherein the RCA product is fragmented specifically in the section L' yielding a fragment comprising a part of L', B', R, A' and further part of L'. This fragment can be sequenced, e.g. starting from L' and/or A' and/or B'.

FIG. 26 D shows yet another option for determining the sequence of the target nucleic acid RCA product, wherein the RCA product is not fragmented. This nucleic acid molecule can be sequenced, e.g. starting from L' and/or B'.

DETAILED DESCRIPTION OF EMBODIMENTS

Figure 1:
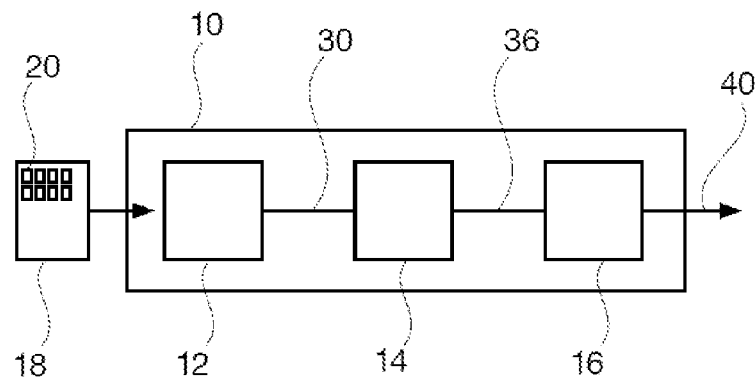
FIG. 1 shows a schematic diagram of a sequencing device according to an embodiment of the invention.

FIG. 1 shows a schematic diagram of a sequencing device or system 10. The sequencing device 10 comprises a sequencing unit 12, a pre-processing unit 14 and an alignment unit 16. The three units 12, 14, 16 may be separate devices that are connected via communication links, but may also be modules of one device 10. In particular, the sequencing unit 12 and a pre-processing unit 14 may form one device and may be situated in one housing and the alignment unit 16 may be a further computer or system that evaluates the output of the device 12, 14.

FIG. 1 further shows a microarray 18 with a plurality of sites or spots 20. Each spot 20 contains a plurality of the same probe molecules or capture molecules or oligonucleotides that are adapted to capture a specific sequence of a fragment of nucleic acids. In particular, the capture probe may be adapted to catch (or hybridize) a fragment of nucleic acids from the target region of the genome. Capture probes used for targeting a section of a genome should be unique for just the target region, otherwise fragments from outside the target region may be captured.

Alternatively, the device 10 is adapted of receiving a substrate 18 with a plurality of microcarriers 20 to which capture probes are attached. The microarray 18 or the microcarriers 20 may be provided with labels (for example a bar code) which may be read by the unit 12. For example, a spot 20 of the microarray 18 may have a label encoding for the probe in the spot 20.

For determining a sequence of nucleotides for a nucleic acid sample, the nucleic acid sample is split into fragments of nucleic acids, which after then may be amplified by PCR and placed in contact with the spots 20 or near the microcarriers 20. The capture probes then hybridize with the fragments of nucleic acids.

After that, the substrate 18 or microarray 18 is put into the sequencing unit 12, which sequences the fragments of nucleic acids. For example, nucleotides with fluorescent groups are bound to a fragment of nucleic acids and the sequence of nucleotides may be determined by detecting the light emitted by the fluorescent groups. This may be done by a controller of the sequencing unit 12 that in the end generates for each fragment of nucleic acids a sequence of identifiers for nucleotides 32 (see FIG. 2).

The operation of the sequencing device 10 will be further described with reference to FIG. 2 and FIG. 3.

Figure 2:
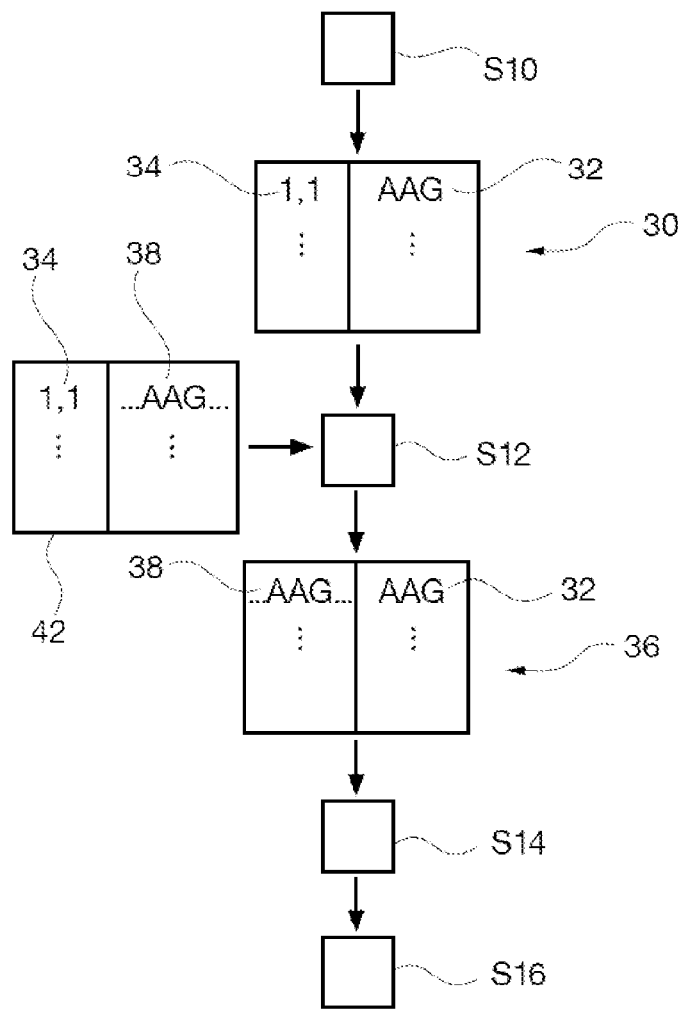
FIG. 2 shows a flow diagram for a method for providing nucleotide sequence data according to an embodiment of the invention.

FIG. 2 shows a flow diagram for a method for providing enriched nucleotide sequence data 36.

In step S10, the sequencing unit 12 generates basic nucleotide sequence data 30 for each fragment of nucleic acids by associating the sequence of identifiers 32 of the fragment of nucleic acids with probe data 34 of the capture probe adapted to capture the fragment of nucleic acids. The probe data may comprise position 34 data which may encode the x- and y-position of the spot 20, the capture probe is situated in. However, the probe data may also comprise the label of a microcarrier 20. In the following, embodiments with position data are provided. However, in the following embodiments, the position data may be replaced by label data.

In particularly preferred embodiments of the invention the position data comprises the x-/y-position of the capture probe on a substrate, which may be a microcarrier such as a microarray or another substrate to which probes may bind or may be bound.

In general, basic nucleotide sequence data 30 (and also enriched nucleotide sequence data 36 and intermediate nucleotide sequence data 50, see below) may comprise a plurality of reads, wherein a read may be a record or a section in the nucleotide sequence data 30, 36, 50 that is associated to one fragment of nucleic acids. In other words, one read may comprise the probe data and the determined sequence of one fragment of nucleic acids.

Each read may comprise a header and a body. The header may comprise the probe data 34 and the body may comprise the determined sequence of identifiers 32. The body may also contain quality information of the sequencing data, i.e. the determined sequence.

The nucleotide sequence data 30, 36, 50 may be in text format and may be stored in a text file. The reads may be sections in the text file. For example, the sequence of identifiers 32 may be a text string comprising the identifiers A, C, G, T of DNA nucleotides. It has to be understood that all sequences of identifiers in this application are example sequences that are templates for real sequences.

At the end of step S10, the basic nucleotide sequence data 30 is then output to the pre-processing unit 14.

In step S12, the pre-processing unit 14, which receives the basic nucleotide sequence data 30, generates enriched nucleotide sequence data 36 for each fragment of nucleic acids. By doing so, the sequencing device 10 may use the a-priori information available by the capture/hybridization probe that has captured a fragment of nucleic acids. The basic nucleotide sequence data 30 may be enriched with an expected sequence 38 or a reference thereto. The expected sequence 38 may comprise a sequence of identifiers for nucleotides that are expected for the sequence of identifiers 32 of the specific fragment of nucleic acids. For example, the expected sequence 38 may start with the above mentioned reference sequence captured by the capture probe. It is to be understood that the sequence of the capture probe is at least partially complementary to the sequence of the fragment of nucleic acid. This means that the probe, which corresponds to the sequence of a probe region on the reference genome, may capture a fragment of nucleic acid as defined herein above. Hence, the sequence of said capture probe is capable of capturing the fragment of nucleic acid by hybridization. It is thus conceivable that one part of the captured fragment, which has hybridized, is expected to be at least partially complementary to the sequence of the sequence of the capture probe. The remaining part of the capture fragment is determined by sequencing and is expected to be equal or similar to the expected sequence.

It will be immediately appreciated by the skilled person that variations such as single nucleotide polymorphisms (SNPs) between the determined sequence of the captured fragment and the expected sequence (38) as defined herein may occur. Thus, in order to determine the variations, only the determined sequence of the captured fragment and not the sequence of capture probe is compared to the expected sequence by sequence alignment. It is to be understood that the sequence of the capture probe is therefore not the same as the expected sequence (38). In order to be able to carry out such a sequence alignment, each determined sequencing data (read) may be enriched with the expected sequence 38 as follows.

The pre-processing unit 14 may determine an expected sequence 38 of the fragment of nucleic acids by converting the position data 34 into the expected sequence 38 with information interrelating the position or the label of the capture probe and the expected sequence 38.

In particular, the pre-processing unit may comprise a data table 42 interrelating position data 34 or label data 34 with expected sequence 38. The expected sequence 38 may be determined from the data table 42, which comprises records linking position data 34 or label data 34 and an associated expected sequence 38. In the data table 42, the positioning of the capture probes on the microarray 20 or the capture probes associated with a certain microcarrier 20 may be encoded. For example, the microarray 20 may comprise a chip or a label like a barcode in which the relationship between a spot 20 and the reference sequences or the expected sequence 38 associated with the capture probes in the spot 20 is stored or encoded. The pre-processing unit may read this information from the microarray 20 and may generate the data table 42 from this information.

However, it is also possible that the data table 42 is generated in another way. For example, if always the same type of microarray 20 is used, the data table 42 may be predefined and stored in the pre-processing unit 14.

At the end of step S12, the enriched nucleotide sequence data 36 is output to the alignment unit 16. The enriched nucleotide sequence data 36 comprises the determined sequence of identifiers 32 and the expected sequence 38 or a reference to the expected sequence. It has to be understood that the nucleotide sequence data 36 does not necessarily comprise the position data 34 or the label data 34.

In the steps S14 and S16, the alignment unit 16 aligns the enriched nucleotide sequence data 36 for each fragment of nucleic acids to a reference nucleotide sequence, for example the sequence of a genome stored in a database. The results 40 of the comparison may be used for SNP calling and/or SNV, structural nucleotide variant, determination.

In step S14, the alignment unit 16 aligns the determined sequence 32 to a reference nucleotide sequence by checking for an exact match of the expected sequence in the reference nucleotide sequence with the determined sequence 32.

In general, aligning may be a mapping of the determined sequence to the reference nucleotide sequence. The mapping may be an exact mapping or an approximate mapping. In step S14, an exact mapping is determined. For example, an exact match may be checked by string comparison of the determined sequence 32 of identifiers with the expected sequence of identifiers 38.

With step S14, the alignment process may be improved using a priori information, if instead of performing only a regular alignment algorithm a string match comparison is first made, to see if the determined sequence matches the expected sequence. This is due to the fact that a string match comparison is a much faster process (in software) than a standard alignment algorithm which involves a more complex approximate matching process. Furthermore, most of the reads will match the reference.

In step S16, the alignment unit aligns the determined sequence 32 to a reference nucleotide sequence by performing a regular alignment algorithm, if no exact match is found for the expected sequence 38. In step S16, only an approximate match may be found.

Summarized, during the alignment process the expected sequence 38 may be used by first checking in step S14 for an exact match and if no exact match (for say the remaining 10% of the initial sequencing reads) is found by second performing a regular alignment algorithm (which may be much more time consuming than comparing for an exact match).

Figure 3:
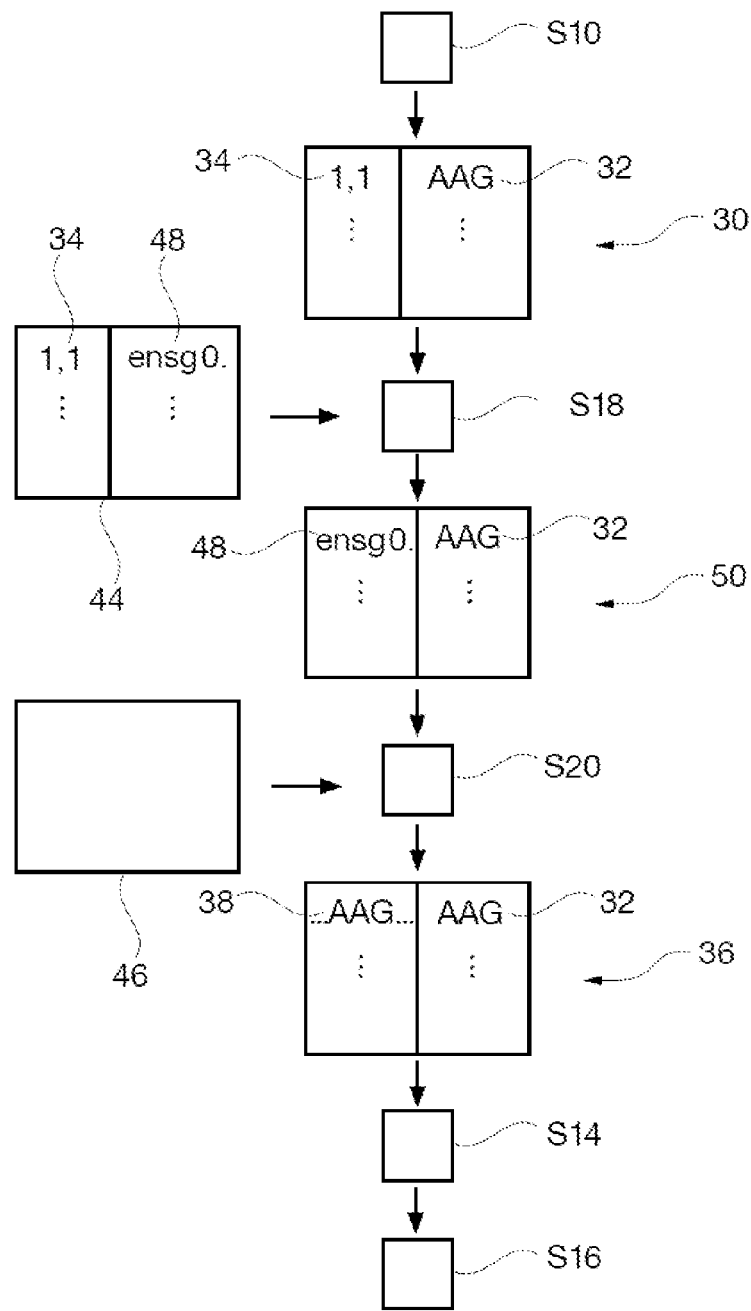
FIG. 3 shows a flow diagram for a method for providing nucleotide sequence data according to a further embodiment of the invention.

FIG. 3 shows a flow diagram for a method for providing enriched nucleotide sequence data 36. The method of FIG. 3 differs from the method of FIG. 2 in that the step S12 performed by the pre-processing unit 14 is replaced by the two steps S18 and S20.

In the case shown in FIG. 3 the pre-processing unit may use two data tables 44, 46 (or a data table 44 and a database 46) to perform the conversion of the position data 34 into the expected sequence 38. To arrive at the solution of FIG. 2, the data tables 44, 46 may be combined into one table 42, which directly relates the x-, y-position 34 or the label data 34 to the expected sequence 38.

Similar to FIG. 2, the pre-processing unit 16 may use information from the microarray 18 or the microcarrier 20 to generate the data table 44 from this information. It may be also possible that the data table 44 is predefined and stored in the pre-processing unit 16.

In a further aspect, the current invention relates to a method for determining the sequence of a target nucleic acid molecule linked to genomic position information of said target nucleic acid molecule. Said method provides sequence information and/or probe data which may be used to determine an expected sequence of a target nucleic acid, wherein said probe data or obtained sequence information is converted into an expected sequence with the help of additional information interrelating the probe data and the expected sequence. The additional information interrelating the probe data and the expected sequence may be derived from a sequence label, preferably an artificial sequence label, and adjacent sequences corresponding to target nucleic acid sequences as present on capture oligonucleotides.

Said method for determining the sequence of a target nucleic acid molecule linked to genomic position information of said target nucleic acid molecule comprises, in a general embodiment, the steps of:

providing a capture oligonucleotide probe which comprises two portions which are complementary in sequence to portions of the target nucleic acid, wherein said portions of the capture oligonucleotide probe are separated by a non-target complementary sequence label;

hybridizing said capture oligonucleotide probe with a sample comprising a nucleic acid molecule, wherein said nucleic acid molecule comprises a sequence which is at least partially complementary to the capture oligonucleotide probe;

circularizing said nucleic acid target molecule by use of a polymerase activity;

amplifying said circularized nucleic acid target molecule, preferably by rolling circle amplification;

determining the sequence of the amplified nucleic acid target molecules by generating a sequence read of at least 2 nucleotides;

identifying the sequence of the non-target complementary sequence label;

identifying the nucleotide sequence of the capture oligonucleotide probe adjacent to the non-target complementary sequence label, wherein optionally 3' and 5' adjacent sequences are individually identified;

identifying the location of the sequence of the capture oligonucleotide probe on a reference genome; and providing a combination of (i) the determined sequence of the nucleic acid target and (ii) information on its location on a reference genome.

In a specific embodiment of the invention, the method for determining the sequence of a target nucleic acid molecule linked to genomic position information of said target nucleic acid molecule comprises comprises the following steps:

providing a capture oligonucleotide probe which comprises two portions which are complementary in sequence to portions of the target nucleic acid, wherein said portions of the capture oligonucleotide probe are separated by a non-target complementary sequence label, and an immobilization moiety;

hybridizing said capture oligonucleotide probe with a sample comprising a nucleic acid molecule, wherein said nucleic acid molecule comprises a sequence which is at least partially complementary to the capture oligonucleotide probe;

immobilizing said capture oligonucleotide probe-target nucleic acid complex on a solid phase;

removing non-bound nucleic acid molecules form the solid phase;

circularizing said nucleic acid target molecule by use of a polymerase activity;

amplifying said circularized nucleic acid target molecule, preferably by rolling circle amplification;

determining the sequence of the amplified nucleic acid target molecules by generating a sequence read of at least 2 nucleotides;

identifying the sequence of the non-target complementary sequence label;

identifying the nucleotide sequence of the capture oligonucleotide probe adjacent to the non-target complementary sequence label, wherein optionally 3' and 5' adjacent sequences are individually identified;

identifying the location of the sequence of the capture oligonucleotide probe on a reference genome; and providing a combination of (i) the determined sequence of the nucleic acid target and (ii) information on its location on a reference genome.

The term "genomic position information" as used herein refers to a starting point and a direction (5' or 3') on a standardized genome sequence map, or in a standardized genome sequence or sequence database. The genomic position may accordingly be a position within a specific genome, for example, a human, higher eukaryotic, lower eukaryotic, bacterial, viral, or plant reference genome. The position information may comprise at least as much information that a skilled person is enabled to deduce the molecular sequence around the indicated position, or starting from said position. In case of insertions, deletions, rearrangements, transpositions etc., a position in one genome may not necessarily be the same position in a further, different genome, e.g. of the same species or populuation group, or of a different species or population group. Such differences may be indicated, signalled and, if possible, covered by the provision of offset data or transposition data. The position information may be present in any suitable format or form known to the skilled person.

A "capture probe" as used herein relates to an oligonucleotide molecule (or a part thereof), which binds specifically to a complementary nucleotide sequence. The oligonucleotide molecule may, for example, be immobilized on a substrate such as a microcarrier, e.g. a microarray, or a bead or any other suitable entity. The capture probe may also be freely moveable, and/or comprise elements, which allow an immobilization during a hybridization procedure. In specific embodiments of the invention, the capture probe may be randomly immobilized on a solid phase support such as a flow cell. This support may, for example, comprise a polyacrylamide layer, preferably at high density, more preferably at very high density. Further details would be known to the person skilled in the art or could be derived from suitable literature sources such as Bentely et al, 2008, Nature, 456, 53-59 including the supplementary information. In the context of the method for determining the sequence of a target nucleic acid molecule linked to genomic position information of said target nucleic acid molecule as outlined above, the capture probe is preferably a freely moveable entity.

The capture probe may in certain embodiments of the invention comprise functionally different segments. In the context of the method for determining the sequence of a target nucleic acid molecule linked to genomic position information of said target nucleic acid molecule as outlined above, it is preferred that the capture probe comprises at least two portions which are complementary in sequence to portions of a target sequence nucleic acid (see, for example, sections A and B of the capture probe shown in FIG. 23). These portions may vary in length. They may, for example, have a length of 4 nucleotides, or more than 4 nucleotides. For instance, the portion may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or 80 nucleotides or any integer between the indicated values. The preferred lengths of the portions is between about 25 and 30 nucleotides, e.g. 25, 26, 27, 28, 29, 30 nucleotides. The two portions may be of equal length or may show length differences. For example one portion may have a length of 1000%, 700%, 500%, 300%, 200%, 100%, 80%, 70%, 60%, 50%, 40%, 30%, or 20% of the length of the other portion, and vice versa.

Figure 23:
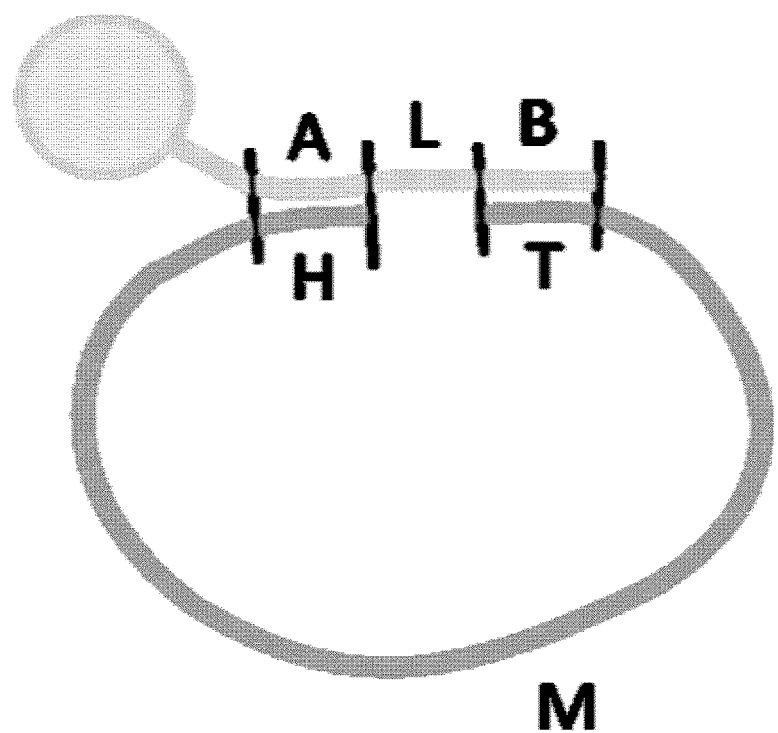
FIG. 23 shows an interaction/binding between a capture probe and a target nucleic acid molecule. The capture probe is created with a part A that is complementary to the head H of the captured target nucleic acid fragment, a part B that is complementary to the tail T of the captured target nucleic acid fragment, and an easily identifiable sequence label L. Section M designates a central portion of the target nucleic acid molecule, which is not complementary to either A or B.

The term "complementary" as used within the context of the capture probe portions refers to the complementarity of the entire portion with a corresponding target sequence. Thus, a portion may be complementary to a target sequence, if all nucleotide bases hybridize to a cognate nucleotide (G-C, and A-T). In further embodiments, the complementarity may also be partial. Such partial complementarity may include a fraction of the nucleotides of the binding portion, e.g. about 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, 60%, or 55%, which hybridize to cognate nucleotides. The complementarity may also be a partial complementarity such that only a stretch of the binding portion fully hybridizes to a target sequence, whereas a further stretch or segment does not hybridize or only partially hybridizes. The two portions (e.g. portion A or B as illustrated in FIG. 23) may, in certain embodiments, have different degrees of complementarity, e.g. portion A may have a partial complementarity of 99%, 98%, 97%, 96%, 95%, 94%, 93%, 92%, 91%, 90%, 89%, 88%, 87%, 86%, 85%, whereas the other portion, e.g. portion B, may have 100% complementarity, or vice versa. In certain embodiments, both portions may have 100% complementarity or may have less than 100% complementarity. If both portions have less than 100% complementarity, they may either have the same degree of complementarity, or may have a different degree of complementarity.

The present invention specifically envisages the possibility that target sequences somewhat differ in complementarity from the binding portions of the capture probes, since these differences may reflect molecular modifications or mutations, e.g. SNPs, indels etc. which are diagnostically important and can preferably be detected according to the methodology described herein. The detection of such potential molecular modifications or mutations, e.g. SNPs, indels etc. which are diagnostically important, is, of course, also possible and particularly envisaged in the adjacent sequences of the target nucleic acid (e.g. sequence M as shown in the illustration of FIG. 23).

The sequences of the capture oligonucleotide probe portions, which are complementary in sequence to portions of the target nucleic acid, may be selected thus that they correspond to sections of the target sequence which are known to be at least on the same strand of a nucleic acid molecule, e.g. of a double-stranded genomic DNA molecule. Preferably, said sequence of the capture oligonucleotide probe portions may be selected such that the distance between the complementary sequences in the target sequence may be more than 50 000 nucleotides, about 50 000 nucleotides, about 40 000 nucleotides, about 30 000 nucleotides, about 25 000 nucleotides, about 20 000 nucleotides, about 15 000 nucleotides, about 10 000 nucleotides, about 9000 nucleotides, about 8000 nucleotides, about 7000 nucleotides, about 6000 nucleotides, about 5000 nucleotides, about 4000 nucleotides, about 3000 nucleotides, about 2000 nucleotides, about 1500 nucleotides, about 1000 nucleotides, about 900 nucleotides, about 800 nucleotides, about 700 nucleotides, about 600 nucleotides, about 500 nucleotides, about 400 nucleotides, about 300 nucleotides, about 200 nucleotides, or about 100 nucleotides or less, or any integer between the indicated values.

The sequences of the capture oligonucleotide probe portions, which are complementary in sequence to portions of the target nucleic acid, may further be selected and arranged on the capture oligonucleotide probe such that the target nucleic acid is bound in a padlock manner, e.g. as illustrated in FIG. 23. This can be accomplished by providing the complementary probe portions in a suitable sequential arrangement and directionality (for example as illustrated in FIG. 23, designators A and B). These features can further be adapted to specific genomic situations, e.g. the presence of repetitive sequences, sequence conversions etc.

The assumed distance of the binding portions in the target sequence may be reflected, in specific embodiments, by the composition of the target samples, or its preparation. In principle, a nucleic acid sample to be used within the context of the method for determining the sequence of a target nucleic acid molecule linked to genomic position information of said target nucleic acid molecule as described above may be any sample comprising any amount of nucleic acids, derived from any source, or being of any origin. The sample preferably comprises double- or single-stranded DNA or RNA or both, more preferably double stranded DNA. The sample may comprise entire genomes, or may comprise a fraction or sub-fraction thereof, e.g. after having passed through a fractionation, lysis or purification process. Such processes would be known to the person skilled in the art. The sample may be a prokaryotic, viral or eukaryotic sample. It is preferred that the sample is a eukaryotic sample. The sample may, for example, be a plant tissue sample, a lower eukaryotic sample, or a higher eukaryotic sample. It may, in specific embodiments, be a sample from a mammalian source, more preferably from a human source. Sample acquirement procedures suitable for the present methodology would be known to the skilled person.

For the sample to be usable in the currently described method, it has to be rendered and/or kept single stranded. This can be accomplished by any suitable method known to the person skilled in the art. Typically, the sample comprising DNA or doublestranded nucleic acids may be heated to a temperature at or above the melting temperature, e.g. 60° C., 65° C., 70° C., 80° C., 90° C., or 95° C. In order to keep the nucleic acid in a single stranded form, salt solutions, e.g. SCC and/or SDS or other suitable buffers, ions or compounds may be used. Further sample preparation procedures suitable for the present methodology and additional details would be known to the skilled person and can be derived from qualified literature sources such as Johansson et al, Nucleic Acid Research, 2011, 39(2), e8, 1-13.

In order to be useable for the currently described method, the target nucleic acid molecules in the sample have to be fragmented. The term "fragmenting" as used throughout the description means to include any activity which leads to a breaking, cleavage or shortening of nucleic acid molecules, however without complete or essential degration of the nucleic acid molecules. The fragmentation may be site-specific or random. The fragmentation may, for example, be carried out enzymatically, e.g. by using restriction enzymes, or endonucleases or by transposons (for example as marketed by Epicenter, Madison, Wis., USA, or based on the Nextera DNA Sample Preparation Kit as marketed by Illumina). Alternatively, the fragmentation may be carried out on the basis of physical forces, e.g. by shearing, sonicating or physically breaking the nucleic acid molecules. Suitable methods would be known to the skilled person. It is preferred that the fragmentation is carried out enzymatically. It is particularly preferred to use restriction enzymes or endonucleases for the fragmentation process. Fragmentation may accordingly be carried out by selecting restriction enzymes having a recognition site with a predermiable frequency in a target nucleic acid sample, e.g. binding (and cutting) on average every 50 000 nucleotides, every 40 000 nucleotides, every 30 000 nucleotides, every 25 000 nucleotides, every 20 000 nucleotides, every 15 000 nucleotides, every 10 000 nucleotides, every 9000 nucleotides, every 8000 nucleotides, every 7000 nucleotides, every 6000 nucleotides, every 5000 nucleotides, every 4000 nucleotides, every 3000 nucleotides, every 2000 nucleotides, every 1500 nucleotides, every 1000 nucleotides, every 900 nucleotides, every 800 nucleotides, every 700 nucleotides, every 600 nucleotides, every 500 nucleotides, every 400 nucleotides, every 300 nucleotides, every 200 nucleotides, or every 100 nucleotides or at any integer number in between the indicated values. In certain embodiments the envisaged fragment length may be made dependent on the identity of genetic information to be analysed, i.e. the gene or genomic portion to be sequenced or which is targeted. The envisaged fragment length length may, thus, be adjusted to the size of the gene, the prence and number of introns, the size and distribution of exons, the chromosomal location, the question whether a single gene or a gene cluster is to be analysed etc. In certain embodiments it may thus be advantageous having rather short fragments lengths, e.g. in the range or 1000 nucleotides to 100 nucleotides, or 3000 nucleotides to 500 nucleotides, while in other embodiments it may be advantageous having longer fragments, e.g. fragments in the range of 50 000 to 30 000 nucleotides, or 30 000 to 3 000 nucleotides etc. For such long fragments, it would be advantageous to apply for example, as these methods offer long read length, the real time single molecule technique marketed by Pacific Biosciences or the (biological) nanopore sequencing being developed by Oxford Nanopore Technologies. Further sequencing methods, which provide long ranges would of course also be envisaged by the current invention.

In specific embodiments, one, two, three, 4, 5, 6, 7, 8, 9, 10 or more different restriction enzymes or endonucleases may be used at the same time and/or with one sample or sample aliquot. The identity of the restriction enzymes or endonucleases and/or the combination of restriction enzymes or endonucleases may be selected according to the predetermined or known frequency of their binding motifs in the target nucleic acid or the target genome. Corresponding information would be known to the skilled person and can be derived from suitable textbooks or manufacturer documentation. The use of restriction enzymes or endonucleases may further be combined with the employment of physical forces, e.g. shearing of the DNA.

In specific embodiments of the invention, fragmented target nucleic acid molecules may be provided in one or preferably more than one aliquot, e.g. 2, 3, 4, 5, 6, 7, 8, 9, 10, 11, 12, 15, 20 or more aliquots. These different aliquots may preferably be treated with different restriction enzymes or endonucleases or different combinations of restriction enzymes or endonucleases, or treated under different conditions with identical restriction enzymes or endonucleases, or both. Such different conditions may, for example, be different enzyme concentrations, different periods of incubation, different incubation temperatures, different concentrations of buffers, ions or additional ingredients, the presence or absence of inhibitors etc.

In particularly preferred embodiments of the present invention, the indicated conditions as well as the identity and combination of restriction enzymes or endonucleases may be selected such that fragments are generated which comprise sequences complementary to both binding portions of the capture oligonucleotide probe, preferably at the end of the fragment. It is accordingly preferred that at least one of the complementary regions of the binding portions of the capture oligonucleotide probe is located at the 5' or 3' end of the fragmented target nucleic acid. In case the complementary region of the binding portion of the capture oligonucleotide probe is located internally of the fragment, it is envisaged to additionally use an exonuclease to create opposing nucleic acid ends, which allows for a circularization of the target nucleic acid.

The term "non-target complementary sequence label" as used herein refers to a sequence which is not complementary to the target nucleic acid molecule. The sequence label may, for example, comprise an artificial sequence which is not present in the genomic sequence of the analysed entity or organisms. The length of the sequence label may vary, reaching from about 4 nucleotides to about 500 nucleotides. It is preferred to have sequence labels of 4, 5, 6, 7, 8, 9, 10, 11, 12, 13, 14, 15, 16, 17, 18, 19, 20, 21, 22, 23, 24, 215, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 or 80 or more nucleotides length. The sequence label may preferably have a length of about 60 nucleotides. The sequence of the sequence label may be any arbitrary sequence. It may, thus, vary in dependence on different parameters and/or sample contexts. It may, for example, be adapted to the GC-content of the genome of an organisms, the availability of certain sequences in the genome, the probability of being hybriziable to genomic fragments, folding or structural properties of the nucleic acid, the property of binding or being bound by protein factors or any other suitable parameter known to the skilled person. In a preferred example, the sequence label may comprise 20 G, followed by 1, 2, 3, 4, 5 or more T, followed by 20 G. Alternatively, the sequence label may comprise 20 A or T, followed by 5 C or G, followed by 20 A or T. Further alternatives, such as 10 G or C, followed by 5 T or A, followed by 10 G or C etc. are also envisaged. Further examples envisaged by the present invention include 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 nucleotides on one side (e.g. the side of portion A of FIG. 23) comprising any one of A, T, G, C, preferably only of one type, i.e. only A, T, G, C, optionally followed by a core segment of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 nucleotides comprising any one of A, T, G, C, optionally followed on the second side (e.g. the side of portion B of FIG. 23) 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 nucleotides comprising any one of A, T, G, C, preferably only of one type, i.e. only A, T, G, C. Further combinations comprising mixtures of A, T, G and C stretches, portions or motifs within the sequence label are also envisaged. The structure and sequence of the non-target complementary sequence label may advantageously be used to demark a boundary between the adjacent sequences and the non-target complementary sequence label, in particular the sequences complementary to target nucleic acids, e.g. sequences A and/or B of FIG. 23. Typically, the sequence label as described herein should not be naturally occurring in the genome or sequence analysed, i.e. should not be encompassed in the target genome or sequence.

In further embodiments of the invention, the non-target complementary sequence label may comprise a recognition site or motif for a restriction enzyme or endonuclease. It is preferred that the recognition site or motif is not present in the target sequence or target genome. Such a recognition site may, for example, be designed in dependence on the information on the reference genome of the organism whose sequence is to be determined. Further possibilities include the provision of artificial recognition sites and cognate modified restriction enzymes. In further embodiments of the invention, the non-target complementary sequence label may comprise a sequence or motif which is structurally labile or shows a tendency to break, allowing for an increase of breakage in the sequence label upon the use of shearing forces as described herein.

In further embodiments, the non-target complementary sequence label may additionally comprise a barcode sequence. This barcode sequence may be any arbitrary or non-natural sequence, e.g. an artificial sequence. The barcode sequence may have any suitable length, e.g. a length of 5 nucleotides, 6, 7, 8, 9, 10 or more nucleotides. This sequence may be used, for example, diagnostically to identify sample origins, patient origins, patient group origins, organ or tissue sources etc.

In a preferred embodiment, identical non-target complementary sequence labels may be used for a sequencing approach with more than one set of capture oligonucleotide probes, thus allowing for the identification of the label by only localizing one specific sequence in the determined sequence information. In further embodiments, more than one non-target complementary sequence label may be used, e.g. 2, 3, 4, 5, 6, 7, 8, 9 or 10.

In further embodiments, the non-target complementary sequence labels may be combined with barcode sequences, which should be different for every patient, organ source, tissue source etc. analyzed. Also a combination of different label sequences and different barcode sequences is possible.

An "immobilizing moiety" as mentioned herein refers to any moiety which is suitable for connecting the capture probe to a substrate. Examples of such moieties are biotin, avidin, streptavidin, amine groups etc. It is preferred to have a biotin moiety on the capture probe. This can effectively be bound by avidin, streptavidin etc. located on a solid phase or substrate. Further alternative binding possibilities, which are also envisaged here, would be known to the skilled person.

The term "hybridize" as used throughout the application relates to a binding or capturing of capture probe and target nucleic acid molecules. This binding interaction depends and/or may be modulated by conditions in the environment of the binding partners. Such conditions are and/or are selected from: buffer concentrations, buffer ingredients, pH, presence and concentration of formamide, presence and concentration of one or more ions, in particular cations, presence and concentration of EDTA, presence and concentration of one or more salts, in particular NaCl, the temperature of the binding environment, the time of interaction, liquid movement and its degree, the possibility of complementary interaction, the degree of mismatches between the interaction partners etc. In a typical hybridization situation, the environment may comprise 0%-50% formamide, 0.7-1 M NaCl, 3 mM-5 mM EDTA, preferably 3.5 mM EDTA, and optionally SDS or Tween, e.g. 0.05%-0.1% Tween-20, or lawoylsarcoore (soap) at 0%-1%. The hybridization temperature may be set, for example, to about 40° C. to 75° C., e.g. about 75° C., 68° C., 62° C., 55° C., 46° C. etc., or any combination of these temperatures in time intervals, e.g. 20-40 min 75° C., followed by 20-40 min 68° C., followed by 20-40 min 62° C. followed by 20-40 min 55° C., followed by 20-40 min 46° C. etc. The hybridization parameters may be varied in dependence on an immobilization step.

The hybridization may in further specific embodiments be accompanied or followed by one or more washing steps. These washing steps may lead to a removal of non-bound nucleic acid molecules. The remaining nucleic acid molecules preferably comprise only or essentially capture oligonucleotide:target nucleic acid complexes, e.g. bound on a solid phase or substrate. It is, in this embodiment, preferred to combine the immobilization of the capture probe as defined herein above with the subsequent removal of non-bound, i.e. not directly or indirectly (e.g. over a binding the immobilized entity) immobilized nucleic acid molecules or derivatives thereof.

In a further, alternative embodiment, the selection approach implemented by the provision of immobilization moieties and removal steps may be performed by a selection of nucleic acid sequences comprising the non-target complementary sequence label (e.g. sequence label L as shown in FIG. 23). This selection may, for example, be performed via a computational or bioinformatics approach by filtering available sequence information for the presence of said non-target complementary sequence label. In specific embodiments of the present invention sequence information for all available nucleic acid molecules may be obtained (i.e. there may not be any immobilization and removal step), followed by a selection of sequences via software or bioinformatics filtering or searching for the non-target complementary sequence label as defined herein. Thereby a corresponding subgroup of all available sequence reads may be obtained, which may be further analysed according to the methods described herein, or parts thereof.

A "circularization" step as mentioned herein above relates to the closing of a gap, which is produced by the presence of the non-target complementary sequence label (see also FIG. 23). Such a circularization step may be carried out by any suitable activity. It is preferred that the circularization by performed by a polymerase activity, e.g. Taq polymerase, or any proofreading polymerase such as Pfu polymerase. Further suitable polymerases as well as suitable conditions would be known to the skilled person and can be derived from qualified literature sources such as Hubscher et al, DNA Polymerases: Discovery, Characterization and Functions in Cellular DNA Transactions, 2010, $1^{st}$ ed, World Scientific Publishing Co.

In further embodiments of the present invention, the circularization may be carried out by ligating the target nucleic acid ends. This ligation may be carried out by either directly ligating the target nucleic acid termini, or by indirectly ligating the target nucleic acid termini. An indirect ligation may include the binding of an oligonucleotide complementary to the non-target complementary sequence label as defined herein and the subsequent ligation of the oligonucleotide termini to the target nucleic acid ends. The ligation process may also be combined with or additionally include polymerase activities, e.g. if non completely filling oligonucleotides are used.

The amplification of the circularized molecule may be carried out with any amplification means known in the art. The amplification may, in preferred embodiments, be performed with the help of primers. The amplification may, in specific embodiments, be carried out directly after the circularization step. Alternatively, a washing or removal and/or inhibition step may be included. Thus, the amplification may essentially be a PCR, RCA or MDA amplification. It is preferred to carry out the amplification by Rolling Circle Amplification (RCA). RCA results in a linear concatemeric amplification product comprising multiple copies of the complement of the template sequence. It is preferred that during the RCA the capture oligonucleotide probe be used as starting primer. Alternatively, one or more further primer oligonucleotides, which may bind at different positions, may be used. Enzymes to be used for RCA would be known to the skilled person. Preferably phi29 polymerase may be used for RCA. Further parameters and conditions for RCA would be known to the skilled person and/or can be derived, for example, from qualified literature sources such as as Johansson et al, Nucleic Acid Research, 2011, 39(2), e8, 1-13.

Subsequent to the Rolling Circle Amplification (RCA) it may, in certain embodiments of the present invention, become necessary to split, disintegrate or fragmentate the concatemeric RCA product(s). The process may be carried out according to any suitable procedure. For example, a fragmentation of the concatemeric RCA product(s) may be performed such that a random fragmentation along the entire RCA product occurs. This could be accomplished by using physical forces such as shearing forces etc. as described herein above. The shearing process may, in certain embodiments, be adjusted such that a certain minimum or maximum fragment length, or a certain average fragment length is obtained.

In a further embodiment the fragmentation of the concatemeric RCA product(s) may be performed by specifically splitting or breaking the RCA product(s) in the sequence label portion as described herein (see, for example, designator L in FIG. 23). Such as specific splitting may be accomplished by using restriction enzymes or endonucleases having a cognate recognition site or motif in the non-complementary sequence label, e.g. as defined herein. Alternatively, the splitting or breaking may be accomplished by using shearing forces on the sequence label, which comprises a structurally labile section, e.g. as defined herein, prone for breaking upon the application of physical forces such as shearing or sonication etc.

In yet another embodiment, the RCA product may be used without having fragmentated it at all, or alternatively by only having fragmentated a portion of the concatemers, e.g. according to the above described procedures.

In a further step the sequence of the amplified nucleic acid target molecule is determined. The term "determining the sequence of the amplified nucleic acid target molecule" as used herein refers to the process of determining the sequence information of the target nucleic acid by the performance of nucleic acid sequencing reactions. These methods may comprise additional steps such as nucleic acid isolation, transfer, purification or additional amplification steps. Whether and which such additional steps are required may depend on the concrete sequencing method performed. The current invention envisages a corresponding modification of the method steps in dependence on the manufacturers' protocols pertinent to the sequencing approaches. It is preferred that the determination of the sequence of the amplified nucleic acid target be adapted to the state of the amplification product. In case an RCA product is present, the sequence determination should be adjusted to the state of fragmentation of the RCA product and/or the process used for RCA product fragmentation, as defined herein above. Accordingly, adapted primer sequences or different sequencing methods may be used. The read lengths may further accordingly be adjusted. For example, if the RCA product is not fragmented, a longer read may be required.

In addition, the analysis of the outcome of the sequence determination, e.g. the mapping, should be adjusted to the state of fragmentation of the RCA product and/or the process used for RCA product processing or fragmentation.

Methods for sequence determination, as well as corresponding preparatory procedures would be generally known to the person skilled in the art. Preferred are next generation sequencing methods or high throughput sequencing methods. For example, a sequence may be determined by using Massively Parallel Signature Sequencing (MPSS). An example of an envisaged sequence method is pyrosequencing, in particular 454 pyrosequencing, e.g. based on the Roche 454 Genome Sequencer. This method amplifies DNA inside water droplets in an oil solution with each droplet containing a single DNA template attached to a single primer-coated bead that then forms a clonal colony. Pyrosequencing uses luciferase to generate light for detection of the individual nucleotides added to the nascent DNA, and the combined data are used to generate sequence read-outs. Yet another envisaged example is Illumina or Solexa sequencing, e.g. by using the Illumina Genome Analyzer technology, which is based on reversible dye-terminators. DNA molecules are typically attached to primers on a slide and amplified so that local clonal colonies are formed. Subsequently one type of nucleotide at a time may be added, and non-incorporated nucleotides are washed away. Subsequently, images of the fluorescently labeled nucleotides may be taken and the dye is chemically removed from the DNA, allowing a next cycle. Yet another example is the use of Applied Biosystems' SOLiD technology, which employs sequencing by ligation. This method is based on the use of a pool of all possible oligonucleotides of a fixed length, which are labeled according to the sequenced position. Such oligonucleotides are annealed and ligated. Subsequently, the preferential ligation by DNA ligase for matching sequences typically results in a signal informative of the nucleotide at that position. Since the DNA is typically amplified by emulsion PCR, the resulting bead, each containing only copies of the same DNA molecule, can be deposited on a glass slide resulting in sequences of quantities and lengths comparable to Illumina sequencing. A further method is based on Helicos' Heliscope technology, wherein fragments are captured by polyT oligomers tethered to an array. At each sequencing cycle, polymerase and single fluorescently labeled nucleotides are added and the array is imaged. The fluorescent tag is subsequently removed and the cycle is repeated. Further examples of sequencing techniques encompassed within the methods of the present invention are sequencing by hybridization, sequencing by use of nanopores, microscopy-based sequencing techniques, microfluidic Sanger sequencing, or microchip-based sequencing methods. Further methods for sequencing which are envisaged by the present invention, as these methods offer long read length, are the real time single molecule technique marketed by Pacific Biosciences or the (biological) nanopore sequencing being developed by Oxford Nanopore Technologies. The present invention also envisages further developments of these techniques, e.g. further improvements of the accuracy of the sequence determination, the read length or the time needed for the determination of the genomic sequence of an organism etc.

A genomic sequence or a sub-genomic sequence or any portion thereof, e.g. a single nucleic acid fragment read, may be obtained in any suitable quality or accuracy. Preferably, an obtained genomic sequence or a sub-genomic sequence or portion thereof may have no more than one error in every 10,000 bases, in every 50,000 bases, in every 75,000 based, in every 100,000 bases. More preferably, an obtained genomic sequence or a sub-genomic sequence or portion thereof may have no more than one error in every 150,000 bases, 200,000 bases or 250.000 bases. The present invention also envisages the preparation or use of sequences having a higher quality due to improvements in the sequencing technology. The present invention is accordingly not bound by any error margins or coverage limits, and instead focuses on the implementation of the target sequence preparation and the sequence information available, prepared and obtained according to suitable contemporary sequencing techniques. Sequencing results may be stored in any suitable format, e.g. in the FASTA or FASTQ format and on any suitable medium known to the skilled person, e.g. a hard drive or solid state data storage.

In a further step of the method the nucleotide sequence of the capture oligonucleotide probe adjacent to the non-target complementary sequence label is identified. The identification may be carried out on the basis of the sequencing data obtained in the preceding step, e.g. provided in the FASTA or FASTQ format. The identification may essentially comprise a searching for the non-target complementary sequence label as described above in the sequence data. Subsequent to having found said sequence label, adjacent sequences may be identified. The term "adjacent sequence" as used herein relates to sequences being 3' and/or 5' to the non-target complementary sequence label within the sequence data obtained from the amplification product. These adjacent sequences may have a length corresponding to the length of the complementary portions of the capture oligonucleotide probe. In addition to the sequence of these adjacent sequences, information on their location or directionality may be acquired, i.e. whether it is a 5' or 3' sequence with regard to the non-target complementary sequence. Thus, in a specific, optional embodiment of the present invention, 3' and/or 5' sequences are identified individually. The term "identified individually" means that the position of the 3' sequence relative to the non-target complementary sequence label is determined independent of information on the 5' sequence, and that the position of the 5' sequence relative to the non-target complementary sequence label is determined independent of information on the 3' sequence. In preferred embodiments, both adjacent sequences, 3' and 5' are obtained, and their position relative to the non-target complementary sequence label and to each other is determined.

In yet another step, the identified sequence of the adjacent regions comprising the complementary portions of the capture oligonucleotide probe may be used to identify a location of the sequence in a reference genome. The "reference genome" as used herein may be any suitable preexisting genome sequence covering the stretch which is identical or similar to identified sequence data or nucleic acid fragment reads. In certain embodiments of the present invention, the reference genome is an essentially complete prokaryotic genome sequence. In preferred embodiments of the present invention the reference sequence is an essentially complete eukaryotic genome sequence. In yet another embodiment of the present invention said reference sequence is an essentially complete viral genome sequence. Examples of prokaryotic genome sequences are bacterial genome sequences as provided or derivable from NCBIs microbial genome project database. Further details may be derived from McNeil L K et al, The National Microbial Pathogen Database Resource (NMPDR): a genomics platform based on subsystem annotation, Nucleic Acids Res., 2007; 35 (Database issue): D347-53. Examples of eukaryotic genome sequences are provided or derivable from NCBI's BioProject or GenomeProject database, which also may include data from the 1000 Genomes project, or the ENCODE project. Examples of viral genome sequences are provided or derivable from NCBI's viral genome resources database, or from Belshaw R et al, The RNA Virus Database, Nucleic Acids Res., 2009; 37 (Database issue): D431-D435. Further preferred is an animal genome sequence, e.g. the genome sequence of domestic or farm animals, e.g. of cat, dog, sheep, cattle, swine, chicken, monkey, rat or mouse. In further embodiments, the genome sequence is a plant genome sequence. e.g. an agricultural crop or fruit, such as corn, potato, wheat, sorghum, rice, cotton, barley, canola, cucumber, soybean, peach, tomato, papaya, or a research model plant such as *Arabidopsis thaliana* or *Brachypodium distachyon* etc. Further details and reference sequence information may be derived from any suitable database, e.g. the PlantGDB database. Particularly preferred is a human genome sequence. Examples are population specific genome sequences, e.g. Caucasian genome sequences, African genome sequences, Asian genome sequences etc. Further examples include subject-specific genome sequences, or consensus sequences thereof, e.g. a master reference sequence comprising a conjunction of individual genome sequences. Further details and reference sequence information may be derived from any suitable database, e.g. the UCSC genome database, or the NCBI human genome resources database. These genome sequences may be essentially complete or comprise sub-portions of an essentially complete prokaryotic, eukaryotic, or viral genome as defined above.

In specific embodiments of the present invention, the reference genome may be a standard genome or a healthy subject's genome showing the genetic constitution of a subject which is not afflicted by a disease. In case a partial reference genome is employed, it may be a standard genome showing the genetic constitution of a subject which is not afflicted by a disease associated with the region of the genome comprised in the partial genome sequence.

In a further, final step a combination of (i) the determined sequence of the nucleic acid target and (ii) information on its location on a reference genome is provided. This combination may be provided in the form of a sequence linked to one or more reference genome position indications, in the form of a sequence linked to a genomic sequence position data table derived from a reference genome.

In a preferred embodiment, the present invention relates to a method for providing nucleotide sequence data as defined herein above, wherein said probe data comprises information on the location of the determined sequence of the nucleic acid target on a reference genome obtainable by the method of determining the sequence of a target nucleic acid molecule linked to genomic position information of said target nucleic acid molecule as defined above, and wherein the expected sequence is defined by interrelating the information on said location on a reference genome with the corresponding sequence of the reference genome. Accordingly, based on the combination of (i) the determined sequence of the nucleic acid target and (ii) information on its location on a reference genome as obtainable by the method for determining the sequence of a target nucleic acid molecule linked to genomic position information of said target nucleic acid molecule outlined above, an expected sequence may be defined which derives the sequence which corresponds to the molecularly determined sequence from a reference genome as mentioned herein. The reference genome may preferably be a standard genome or a healthy subject's genome showing the genetic constitution of a subject which is not afflicted by a disease. Alternatively or additionally, an expected sequence may be defined which derives the sequence which corresponds to the molecularly determined sequence from a reference database comprising sequences differing in known SNPs (single-nucleotide polymorphisms) or SNVs (structural nucleotide variants) from a standard sequence or reference genome sequence. Such variant sequences may comprise or may additionally comprise, for example, signature data specific to a disease or disorder selected from the group comprising missense mutation, nonsense mutation, single nucleotide polymorphism (SNP), copy number variation (CNV), splicing variation, variation of a regulatory sequence, small deletion, small insertion, small indel, gross deletion, gross insertion, complex genetic rearrangement, inter chromosomal rearrangement, intra chromosomal rearrangement, loss of heterozygosity, insertion of repeats and deletion of repeats. In further embodiments, the expected sequence may comprise more than one type of sequence, e.g. a standard or healthy subject's genomic sequence and additionally a sequence comprising known variants of said genomic sequence, wherein said variants are preferably linked to diseases, disease states, symptoms etc.

In step S18, the pre-processing unit 14 converts the position data 34 or label data into a genomic position 48 of the fragment of nucleic acids by reading the genomic position from the first data table 44. The first data table 44 comprises records linking a position data 34 or label data 34 with an associated genomic position 48. In this step, the pre-processing unit 14 may generate intermediate nucleotide sequence data 50 that comprises entries with a genomic position 48 and the associated determined sequence 32. For example, the data table 44 may be a look-up table 44 comprising the x- and y-position of the spot 20, and the x-, y-information may be converted to a genomic position 48 by using the look-up table 44.

The genomic position 48 in the genomic position data 36 may be seen as a software code that is added to the sequenced read 30 which specifies or encodes for the genomic position of the sequenced read 30.

In step S20, the pre-processing unit 14 converts the genomic position 48 into the expected sequence 38 by reading the expected sequence 38 from the second data table 46. The second data table 46 comprises records linking a genomic position 48 with an associated expected sequence 38. Also the second data table 46 may be a simple look-up table 46.

Alternatively, the pre-processing unit 14 may use a reference nucleotide sequence (for example a reference genome) stored in a database 46 to determine the expected sequence.

At the end of step S20, the enriched nucleotide sequence data 36 is formed similar to the method of FIG. 2.

In one case, the expected sequence 38 may comprise a sequence of identifiers for nucleotides.

However, note that in step S12 or step S20, the expected sequence 38 need not code one sequence of identifiers. The expected sequence 38 may code a group of expected sequences differing in known SNPs (Single-nucleotide polymorphisms) or SNVs (structural nucleotide variants) so that all members of the group may be first checked by a direct comparison in step S14. Summarized, the expected sequence may comprise information on variants of the sequence of identifiers.

As already said, the enriched nucleotide sequence data 36 comprises the expected sequence 38 or a reference to the expected sequence 38. The expected sequence 38 or its reference may be seen as a software label or software code that is added to the basic sequence data 30. The expected sequence 38 may be added in the sequencer device 10, in particular in the pre-processing unit 14. In such a way the pre-processing unit 14 may have an output that specifies the probe, which had captured the sequenced fragment.

The software code encoding the expected sequence or its reference does not necessarily have to be based on the 4 nucleotides (A, C, G, T) but may as well be based on other letters, numerals etc.

According to a further embodiment, the pre-processing unit 14 may generate enriched nucleotide sequence data by combining the basic nucleotide sequence data 30 with the data table 42 or the data table 44. For example, the pre-processing unit 14 may output a file or a data stream comprising the basic nucleotide sequence data 30 and a data table 42, 44 linking the position data 34 with a reference to the expected sequence.

Figure 4A:
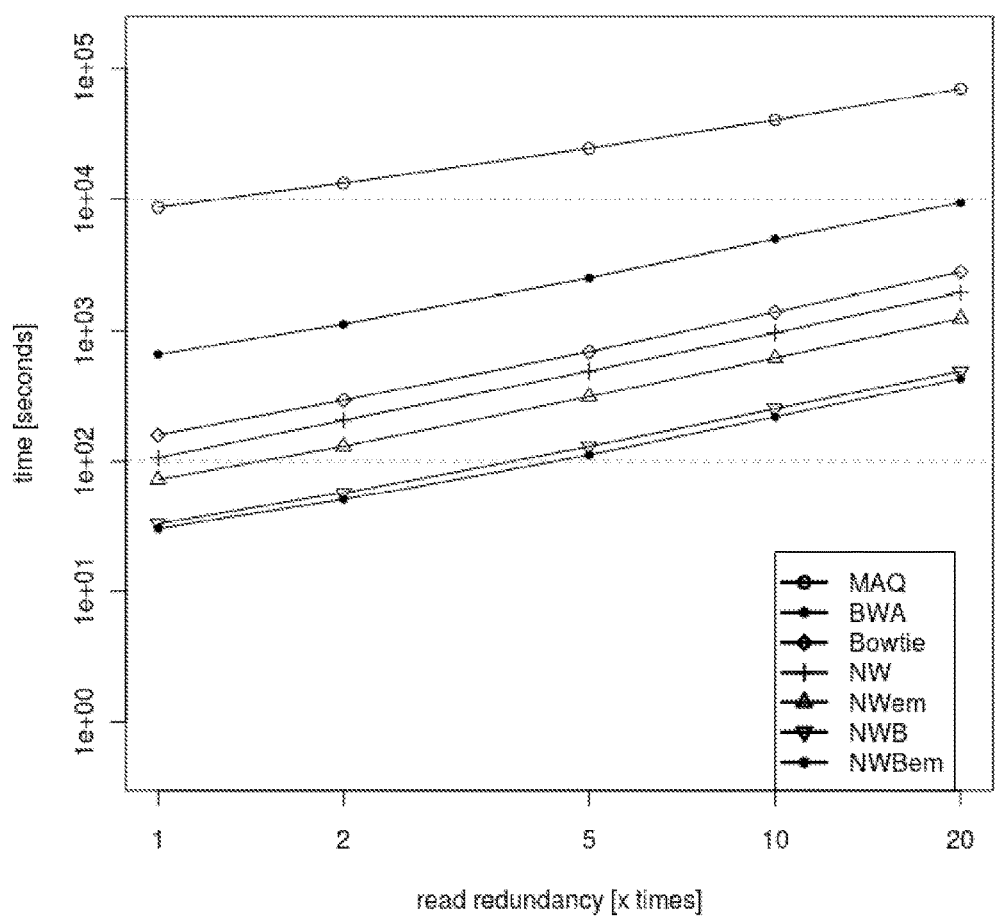
FIG. 4A shows the comparison of the alignment speed of different aligners versus read redundancy. Bowtie, BWA and MAQ aligned against the whole genome; the Needleman-Wunsch implementations used the position information to align to the associated reference sequence. Settings: target size 3 Mb, read length 50 bases, 1% sequencing error, 10% reads off-target. Both axes are in logarithmic scale.

FIG. 4A shows the performance gain due to the method as described in the above and in the following. To evaluate the alignment speed of the approach according to the present invention, the computation times required for aligning targeted sequencing experiments were compared to the performance of regular aligners (Bowtie, BWA and MAQ). These latter aligners do not use the a priori genome position information and align to the whole genome. The diagram of FIG. 4A shows the number of copies per read (x-axis) versus the computation time in seconds (y-axis). The curves depict the computation time for the Burrows-Wheeler Aligner (BWA) 52, the bowtie aligner 54, an implemented Needleman-Wunsch algorithm 56 and an optimized Needleman-Wunsch algorithm (NWem) 58. BWA 52 and bowtie 54 have been aligning against the whole human genome, whilst both Needleman-Wunsch algorithms 56, 58 used the location information. The optimized variant 58 checked for a perfect match via string comparison before the alignment of non-exactly matching sequences. These calculations were performed on a grid of 1648 cores divided over 206 Dell PowerEdge M600 blade servers, each utilizing two Intel Xeon L5420 Quadcore CPUs at 2.5 GHz with 16, 32 or 64 GB of random access memory.

The FIG. 4A show the results of such a comparison for a 3 Mb target region, a read length of 50 bases, a sequencing error of 1% and with 10% reads off-target. These settings correspond to a total of 264,616 reference sequences. Four different implementations of the Needleman-Wunsch algorithm (NW, NWem, NWB and NWBem) were used. As can be seen, MAQ is the slowest of the aligners used in this comparison, with its computation time ranging from 8,713 seconds up to 69,768 seconds depending on the read redundancy. The two Burrows-Wheeler transform based aligners perform the same calculations much faster, requiring 661-9,419 seconds (BWA, ~6.86× faster than MAQ) and 159-2,791 seconds (Bowtie, ~22.9× faster than MAQ) respectively. These results confirm previous observations concerning the alignment speed of Burrow-Wheeler transform based aligners. Nevertheless, the Needleman-Wunsch algorithms using position information lead to considerably shorter alignment times. As compared to Bowtie the computation time is decreased by a factor of ~1.4 for NW (106-1,949 sec), whilst NWem (73-1,244 sec.) even gains factor of ~2.2. This gain increases further for NWB (32-491 sec. or 5.7× faster than Bowtie) and NWBem (30-430 sec. or ~6.6× faster than Bowtie). In conclusion, the total computation time for approximately 53.3 million reads of 50 bases length can be reduced from 46.5 to approximately 7 minutes when adapting a pruned Needleman-Wunsch algorithm to use the a priori information and comparing to the fastest regular aligner Bowtie.

Figure 4B:
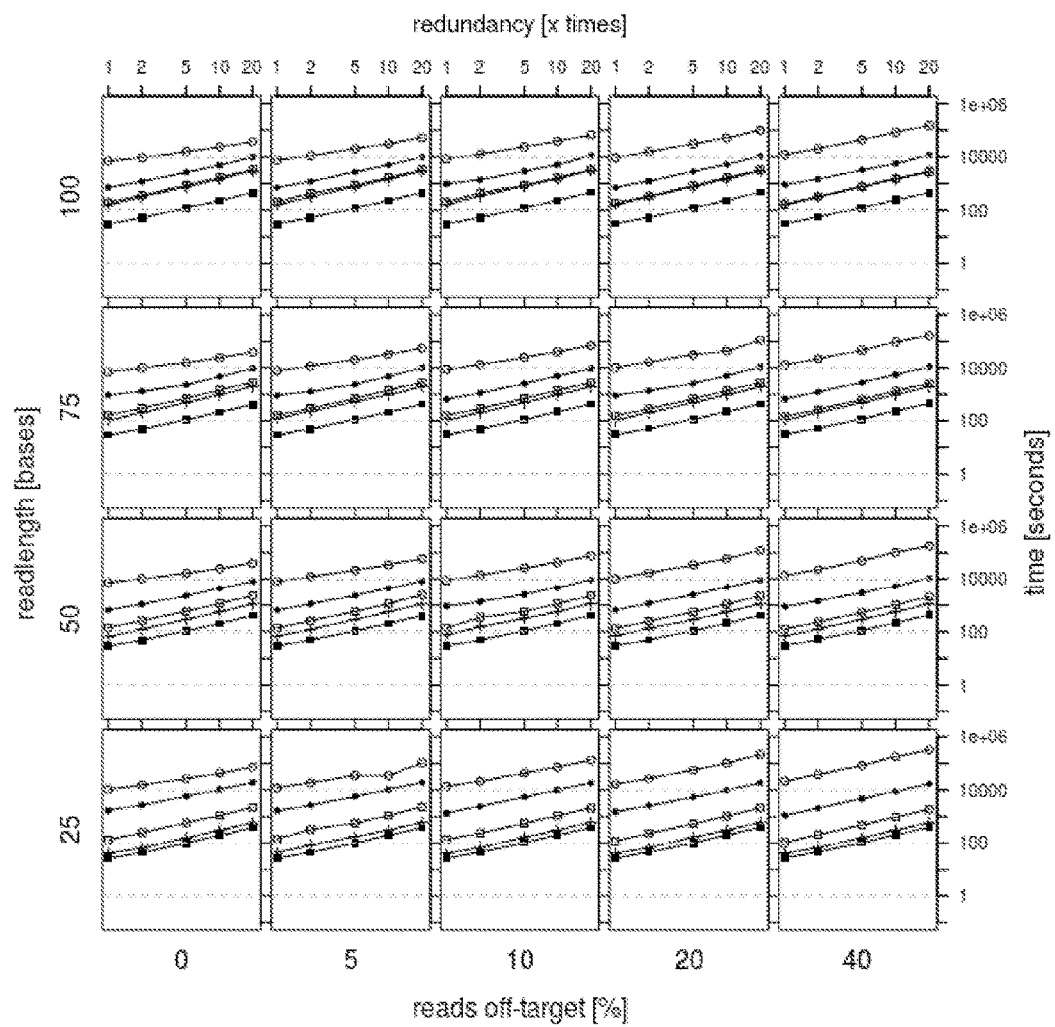
FIG. 4B shows a comparison of different aligners for different read lengths, percentages of reads off-target and read redundancies. MAQ (○), BWA (●) and Bowtie (□) aligned against the whole genome, NW (+) and NWBem (■) used the position information to align to the associated reference sequence. Settings: target size 30 Mb, 1% sequencing error.
Figure 4C:
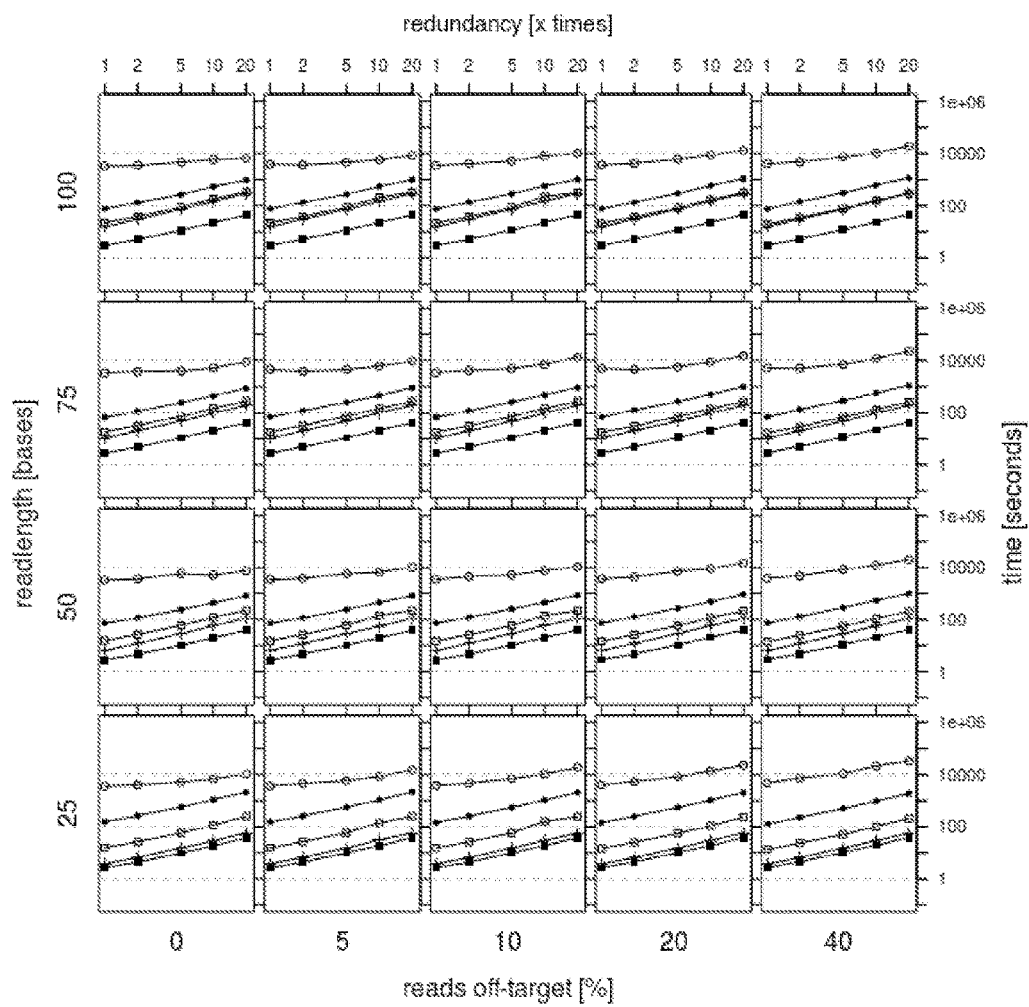
FIG. 4C shows a comparison of different aligners for different read lengths, percentages of reads off-target and read redundancies. MAQ (○), BWA (●) and Bowtie (□) aligned against the whole genome, NW (+) and NWBem (■) used the position information to align to the associated reference sequence. Settings: target size 3 Mb, 1% sequencing error.
Figure 4D:
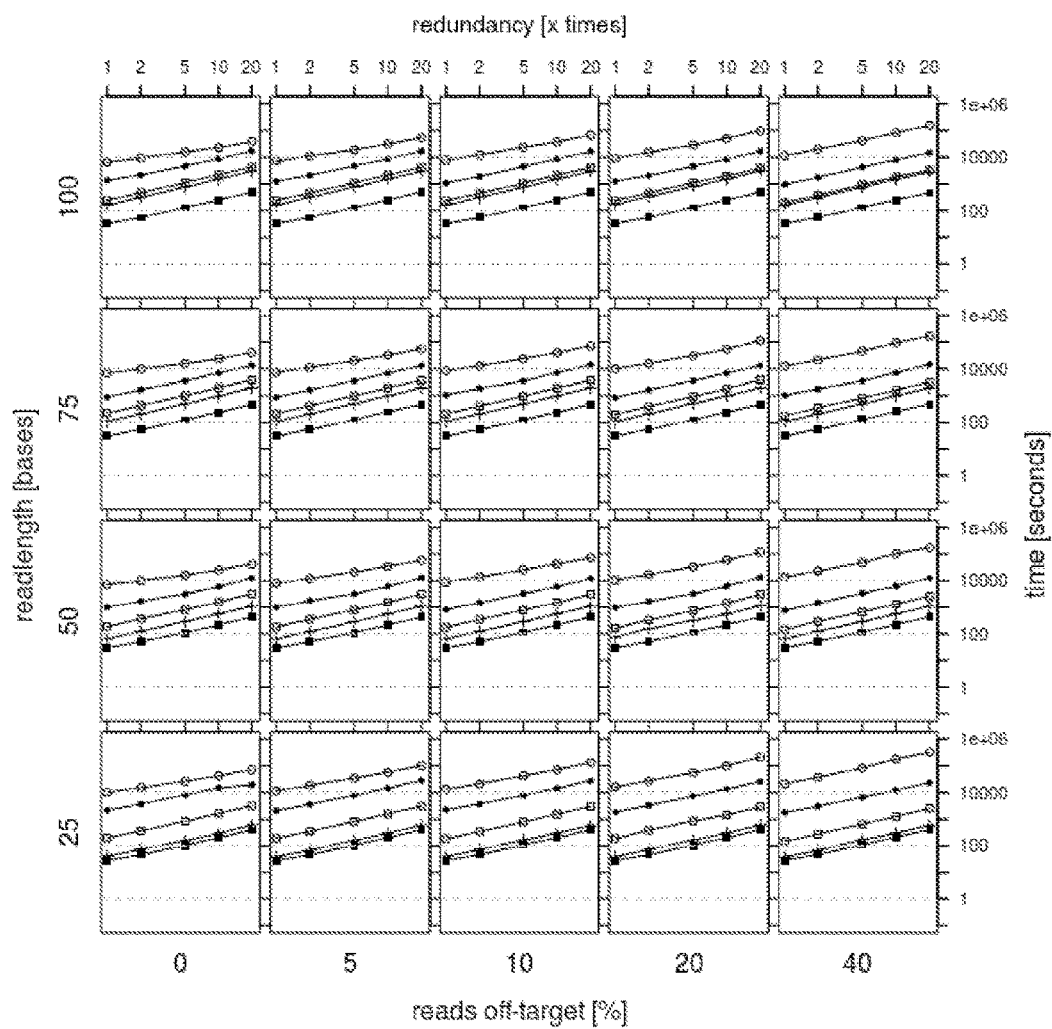
FIG. 4D shows a comparison of different aligners for different read lengths, percentages of reads off-target and read redundancies. MAQ (○), BWA (●) and Bowtie (□) aligned against the whole genome, NW (+) and NWBem (■) used the position information to align to the associated reference sequence. Settings: target size 30 MB, 2% sequencing error.

FIGS. 4B-D show a more extensive comparison of computational experiments, comparing two of the Needleman-Wunsch implementations (NW): the regular Needleman-Wunsch and the banded version of the Needleman-Wunsch algorithm, which is further improved by using direct string comparison (NWBem), for conditions with a sequencing error of 1% per base. FIG. 4A is a subplot of FIG. 4B and can be found in the third row and the third column. When investigating over a broader range of conditions, Bowtie (□) exhibits to be the fastest of the tested common aligners, outperforming MAQ (○) and BWA (●) in every tested parameter combination. Though the use of the position information still leads to a considerable reduction in alignment time, NW shows limitations for longer reads lengths (due to the time complexity of the regular Needleman-Wunsch algorithm being O (max(n,m)3)) which are overcome by NWBem due to pruning of the alignment matrix.

For example, in FIG. 4B, at a length of 100 bases and 40% reads off-target, Bowtie (164-2,765 sec.) and NW (15-2,750) compute on equal levels, whilst NWBem outperforms both (32-447 sec). When considering shorter reads of 25 bases, both NW (42-583 sec.) and NWBem (29-396 sec.) are able to outperform Bowtie (106-1,856 sec). Concerning the amount of reads off-target, Bowtie shows a unique behavior, as the time for aligning is negatively correlated to it, whilst the computation times of all other aligners are positively correlated. This is specifically evident for NWBem, as the exact matching preselection is skipped more often and therefore more reads have to be aligned regularly. It is to be understood that NW performs no preselection and therefore not influenced by this. Thus, Bowtie performs the computations for 100 bases and 0% reads off-target in 193-3,371 seconds and thereby slower, whilst NWBem requires a little less time (32-445 sec.) when compared to the results for 40% reads off-target shown above.

In FIG. 4C, the results for the performance of the aligners for the 3 Mb target region is shown. In case of the 3 Mb target region, the performance gain varies between a factor of ~1.0 to ~4.3 for NW (average: 2.2±1.2) and a factor of ~5.0 to ~7.7 for NWBem (average: 6.8±0.8) when comparing to Bowtie. Similar results can be observed for a 300 kb target region (NW: 2±0.9; NWBem: 6.5±1.1).

In FIG. 4D, the results for the influence of 2% sequencing error per base for the Mb target region at a length of 100 bases and 40% reads off-target are shown. Compared to 1% sequencing error (see FIG. 4A-C), NW (158-2758 sec.) and NWBem (33-460 sec.) seem largely unaffected, whilst Bowtie (196-3,311 sec.) requires ~20% more computation time. Hence, for 2% sequencing error and the 30 Mb target region, the average gain for NWBem increases to 7.8±0.8 compared to Bowtie, whereas for the 3 Mb target region it even reaches a factor of 8±0.8.

Also compared to Bowtie, BWA exhibited a similar behavior, whilst MAQ's performance remained stable. As expected, the amount of reads processed has the biggest impact on the computation time for all of the aligners, with the method according to the present invention showing a behavior similar to Bowtie and BWA. The percentage of sequencing error (in our tests up to 2%) influences the computation time of the common aligners (except for MAQ), whilst it had only a minor effect on the computation time of both NW and NWBem. Nevertheless, this gain in speed is also sensitive to the similarity of the aligned sequences to the expected sequences, as it influences the number of exactly matching sequences. Therefore, both implementations using preselection by exact matching (NWem and NWBem) will benefit from a high specificity in enrichment and a low sequencing error.

FIG. 5A shows a further diagram showing the resulting gain in alignment speed. In FIG. 5, the alignment speed for three different sizes of the target region (300 kb, 3 Mb and 30 Mb) as well as for the whole genome (3.1 Gb) is compared. The last three columns refer to the number of probes. The first row in the diagram shows the size of the target and number of reference sequences. The second row indicates the number of reads. The third row indicates the alignment time.

From FIG. 5A it becomes clear that alignment to just the target region instead of to the whole genome may provide already the biggest gain in alignment speed. However, taking this approach is in practice not possible as none of the so-called target or enrichment methods may be sufficiently accurate. Even the best (using the "selector approach") has only a 92% specificity (typical specificities of other enrichment methods are around 60%), meaning that 8% of the reads do not come from the target region. Forcing also these reads to align to the target region (which one does if one aligns to the target region only) would introduce a significant—and unacceptable—amount of errors, i.e. false positives matches.

When using common enrichment methods, two classes of reads are generated, the first consisting of all reads that originate inside the target region (referred to as ITR), the second comprising all reads that originate outside of the target region (referred to as OTR). When all these reads are aligned solely to the target region, two possible errors may occur that influence subsequent analysis (e.g. SNP calling).

Firstly, OTRs that now align uniquely inside the target region are falsely classified as uniquely matching reads (UMRs) to the target, as they align at a position from which they do not originate (type 1 error). Secondly, all reads (ITR and OTR) that align uniquely inside the target region, but would also align one or more times outside the target region (known as multiple matching reads—MMR) and that would be excluded from analysis, are falsely classified as UMRs as well (type 2 error). Hence, in practice alignment even in targeted sequencing approaches is done to the whole genome.

Therefore only the method based on using the a-priory information, based on which probe has captured a certain fragment which has been sequenced, may allow one to align just to the target region and thereby achieve the gains in alignment speed indicated in FIG. 5A.

Envisaged by the present invention is thus a gain in computation speed by advantageously using a priori information based on the enrichment method for targeted sequencing as described herein. In FIG. 4A-D the presented alignment algorithms are based on dynamic programming and use a priori knowledge to map each read to the expected sequence as defined herein, which is the expected part of the genome. The gain in computation speed was investigated for a total of 900 parameter variations and was observed to range from an average of 6.2±0.8 for a 30 Mb target region to an average of 8±0.8 for a 3 Mb target region when comparing the fastest Needleman-Wunsch implementation (NWBEm) to Bowtie.

FIG. 5B shows the memory requirements for the different aligners, which may vary making great amounts of RAM advantageous or in case of MAQ necessary for the regular aligner when aligning large numbers of reads. NW and NWBem require only a fraction (7.5% to 16.6%) of the memory necessary for the other aligners to perform the calculations when aligning approximately 5 million reads from a 3 Mb target region. It is immediately appreciated by the skilled person that such low hardware requirements combined with the overall speed of the computations would allow to include the alignment within the sequencing device so that post processing of the sequencing data become obsolete.

In specific embodiments of the present invention the alignment algorithm may be exchanged so as to result in a less sophisticated hardware. Envisaged by the present invention is thus the use of a priori information as described herein for minimizing alignment efforts in targeted sequencing. It is to be understood that such reduction of alignment efforts enables the clinical use of sequencing information without the necessity of large computing facilities. For instance, the alignment time of around 7 minutes or less for a targeted resequencing run of approximately 56 million reads would be a technical advantage over conventional sequence alignment methods. Such methods would be especially attractive for the sequencing in clinical use.

Embodiments of the enriched nucleic acid data 36, the intermediate nucleic acid data 50 and the data tables 42, 44, 46 are described with respect to the following figures.

FIG. 6 shows a header 60 for a read in the FASTQ format. FASTQ is a format for sequences from the Sanger institute and is used by the Illumina software, which has a systematic header (identifier) 60. The header comprises the unique instrument name 62, the flowcell line, 64, the tile number within the flowcell lane 66, the x-coordinate 68 of the cluster within the tile, the y-coordinate 70 of the cluster within the tile, the index number 72 for a multiplexed sample (0 for no indexing) and the member of a pair 74, which may be /1 or /2 (paired-end or mate-pair reads only).

Versions of the Illumina pipeline since version 1.4 appear to use #NNNNNN instead of #0 for the multiplex ID 72, where NNNNNN is the sequence of the multiplex tag used for barcoding different samples. The multiplex tag is used when multiple samples are used in the same sequencing run to avoid that the machine is running only at a fraction of its capacity as the sample is sufficiently large to fill the whole flow cell.

FIG. 7 shows a read 76 in the FASTQ format with a header 60 and a body 78. The body 78 comprises a sequence of identifiers 32 that may be generated by the sequencing unit 12 for a specific probe.

Here, the unique instrument name 62 has been replaced by a genomic position identifier 48. The x-, y-coordinates 68, 70 were used to look up in a data table 44 (see for example FIG. 9, 13). The location information comprises the x-, y-coordinates 68, 70 where the probe is placed on the microarray 18. The x-, y-coordinates 68, 70 may also be used to look up a table 42 with sequences (which is shown in FIG. 10) and to choose the corresponding reference sequence 80 to do the alignment with. This could also be done by including information about the location of the probes/references location on the genome into the identifier 48.

The genomic position identifier 48 of FIG. 7 comprises an identifier (ENSG00000110756) for a gene, a start position of an exon (18317546), an end position (18317669) and a chromosome number (11).

In general, the genomic position identifier 48 is adapted to identify a specific position or region in a genome. For example, the genomic position identifier may comprise a start position, an end position and a chromosome number to uniquely identify the region of interest within the genome. This region may be a certain exon, but could also be located anywhere else on the genome, including the extrachromosomal DNA. An identifier for a specific region of the genome (for example for a gene) may also be included in the genomic position identifier for reasons of comprehensibility of the data origin. Of course, permutations of these parameters can also be used.

Note that instead of the reference sequence 80 here and in the following, the complete expected sequence 80 may be encoded in the respective read 76 or table 42, 44, 46.

FIG. 8 shows a read 76 in the FASTA format. A read 76 in FASTA format begins with a single-line description (the header 60), followed by lines of sequence data (the body 78). The description line 60 is distinguished from the sequence data 78 by a ">" symbol as the first character while the string following the ">" symbol is used for identifying the sequence itself and optionally to provide further information.

The header 60 includes the genomic position identifier 48 of the expected sequence 38 as well, in this case the x-, y-coordinates of the capture probe on the microarray 18. The genomic position identifier 48 has been read from a data table 44 (see for example FIG. 9, 13) by using the x-y-coordinates 68, 70.

FIG. 9 shows a look-up table 42, 44 relating the x-y-coordinates 68, 70 with a reference sequence 80 or expected sequence 80 and a genomic position 48. The look-up table 42, 44 is implemented as a multiple entry FASTA file containing all of the used reference sequences 80 or expected sequences 80. The sequences 80 shown all derive from the same exon, but shift by 5 bases to cover it completely.

FIG. 10 shows a look-up table 42 directly relating the x-y-coordinates 68, 70 with a reference sequence 80 or expected sequence 80.

FIG. 11 shows a read 76 in the FASTQ format, similar to the one shown in FIG. 7, in which the genomic position identifier 48 includes the reference position 82. The reference position marks the starting base from which to select the reference sequence 80 to align against as a part/subsequence from the identified target sequence of interest (in this case an exon, see FIG. 12).

FIG. 12 shows a table 46 in FASTA format relating the genomic position 48 with a reference sequence 80 or expected sequence 80 (starting at the reference position 82). The table 46 comprises two records or entries. The reference sequence 80 or expected sequence 80 may be read from the table 46 by taking a subsequence from the whole exon 86, starting from the reference position 82 provided in the header 60 (see FIG. 11) and spanning the exon 86 for the length 84 of the read. It should be noted that FIG. 12 shows an example for an identifier linking to a genomic position that is exonic. However, also non-exonic genomic positions are possible.

FIG. 13 shows an entry of a look-up table 44 relating the x-y-coordinates 68, 70 with a genomic position 48.

FIG. 14 shows an entry of a look-up table 46 relating the genomic position 48 with an expected sequence 80. Also, a reference position 82 of a reference sequence is related to the genomic position 48 and the expected sequence 80.

FIG. 15 shows a read 76 in the FASTQ format comprising a header 60 in which the unique instrument name 62 has been replaced by the reference sequence 80. For example, the x-, y-position 68, 70 may have been used to read the reference sequence from the table 42 of FIG. 10.

FIG. 16 shows a read 76 in the FASTQ format similar to the read of FIG. 11. In the read 76, the genomic position identifier 48 is followed by a reference position 82 of the expected sequence in an exon 86 corresponding to the genomic position 48. The expected sequence starts at the position 82 and ends after the length of the determined sequence 78. In the case shown in FIG. 16, the expected sequence is the sequence of the exon 86 from bases 171-220, due to the read length of 50 bases (first base+ read length−1). The sequence of the exon 86 may be determined from a database or table like the one shown in FIG. 14.

FIG. 17 shows a read 76 in the FASTQ format in which the genomic position identifier 48 is followed by a reference sequence 80.

FIG. 18 shows a read in the FASTA format similar to the read of FIG. 16 with an reference position 82 encoded in the header 60.

FIG. 19 shows a read in the FASTA format similar to the read of FIG. 17 with a reference sequence 80 encoded in the header 60.

FIG. 20 shows an example nucleotide sequence 90 which is encoded in the FASTA format and includes a SNP 92 encoded with "Y". The genomic position 48 relates to a section of gene ENSG00000102468 on chromosome 13 from base 47471072 to base 47471885.

FIG. 21 shows a look-up table 46 similar to the table of FIG. 14. The table 46 of FIG. 21 relates the genomic position 48 with two reference sequences 80. In other words, the reference to the expected sequence is not unique. The two possible variants 94 of the SNP 92 are listed in a separate column.

FIG. 22 shows a read 76 in the FASTQ format similar to the read of FIG. 11. The reference in the header comprising the genomic position 48 and the reference position 82 may be mapped via the table 46 of FIG. 21 to the two variants of the expected sequences based on the SNP 92. Note that the variant 94 of the read sequence is "T".

FIG. 23 shows an interaction/binding between a capture probe and a target nucleic acid molecule as described herein above. The capture probe is created with a part A that is complementary to the head H of the captured target nucleic acid fragment, a part B that is complementary to the tail T of the captured target nucleic acid fragment, and an easily identifiable sequence label L. Section M designates a central portion of the target nucleic acid molecule, which is not complementary to either A or B.

Figure 24:
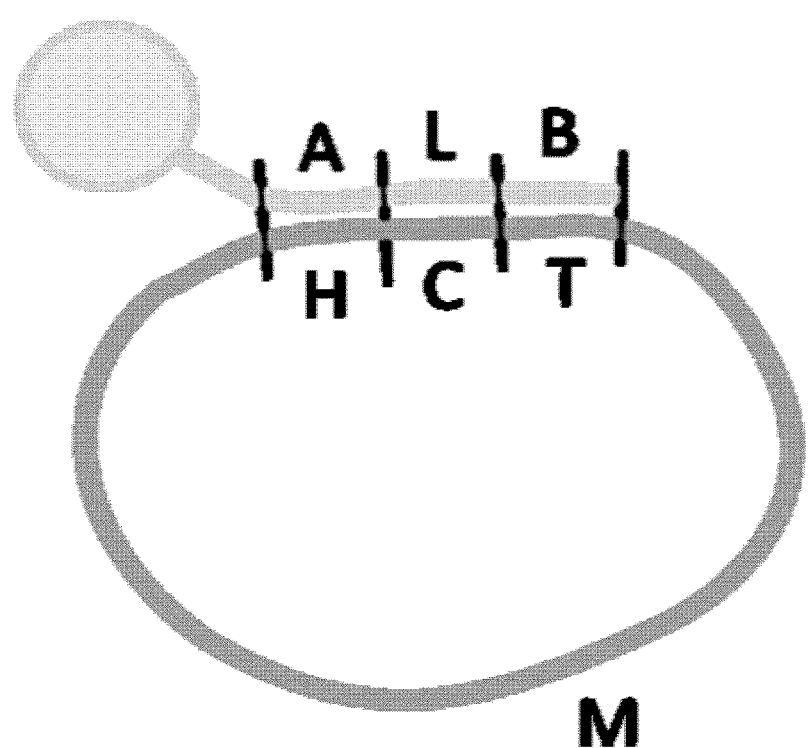
FIG. 24 shows a further step of an interaction process between a capture probe and a target nucleic acid molecule according to the present invention. Subsequent to the interaction shown in FIG. 23 a section C is generated, which is complementary to the easily identifiable sequence label L.

FIG. 24 shows a further step of an interaction process between a capture probe and a target nucleic acid molecule according to the present invention as described herein above. Subsequent to the interaction shown in FIG. 23 a section C may be generated, which is complementary to the easily identifiable sequence label L, as described herein above.

Figure 25:
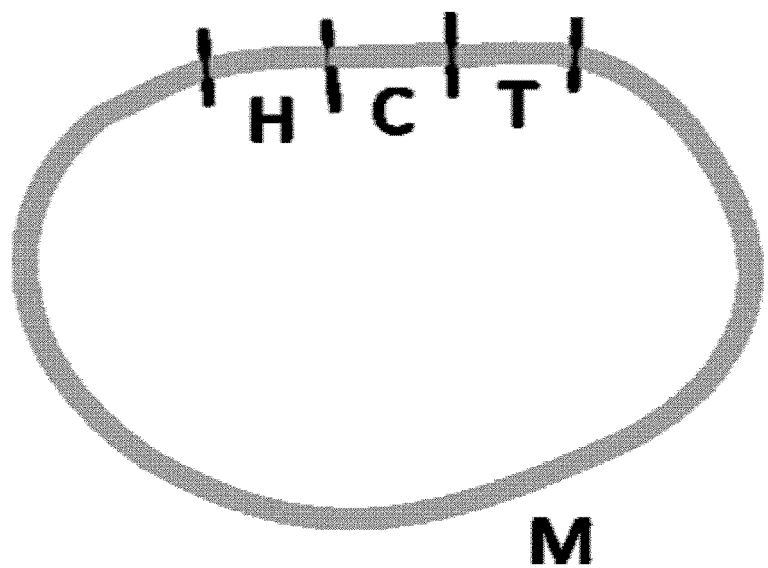
FIG. 25 shows a yet further step of an interaction process between a capture probe and a target nucleic acid molecule according to the present invention. Subsequent to the interaction shown in FIG. 24 the capture probe is removed during amplification process, e.g. via rolling circle amplification (RCA).

FIG. 25 shows a further step of an interaction process between a capture probe and a target nucleic acid molecule according to the present invention. Subsequent to the interaction shown in FIG. 24 the capture probe may be removed during an amplification process, e.g. via rolling circle amplification (RCA). FIG. 25 shows the template which is amplified comprising the head H of the captured target nucleic, the tail T of the captured target nucleic acid fragment, central portion M of the target nucleic acid molecule and section C, which is complementary to the easily identifiable sequence label L.

FIG. 26 shows the potential outcome of a rolling circle amplification (RCA) and the subsequent processing and sequencing steps which may be carried out to determine the sequence of the target nucleic acid fragment. FIG. 26 A shows a potential outcome of a rolling circle amplification of a nucleic acid target fragment shown in FIG. 25 with section A being complementary to section H, section L' being complementary to section C, section B' being complementary to section T and section R being complementary to section M of FIG. 25. FIG. 26 B shows one possible option of determining the sequence of the target nucleic acid RCA product, wherein the RCA product may be randomly fragmented, e.g. as described herein above, yielding a fragment comprising for example, a part of R1, a part of R2, and sections A', L' and B'. This fragment may, in a preferred embodiment, be sequenced with the help of primers, e.g. primers indicated as P1 and P2. The sequencing may, in certain embodiments, provide reads which overlap, thus completely covering section M or R. In other embodiments, the reads may not overlap. The read length may accordingly be adapted to the expected fragment length. FIG. 26 C shows a further possible option of determining the sequence of the target nucleic acid RCA product, wherein the RCA product is fragmented specifically in the section L' as described herein above, yielding a fragment comprising, for example, a part of L', B', R, A' and a further part of L'. This fragment may, in preferred embodiments, be sequenced, e.g. starting from L' and/or A' and/or B'. FIG. 26 D shows yet another possible option for determining the sequence of the target nucleic acid RCA product, wherein the RCA product is not fragmented as described herein above. This nucleic acid molecule may, in preferred embodiments, be sequenced, e.g. starting from sections L' and/or B'.

Summarized, the reference to the expected sequence may be the expected sequence itself, a genomic position and/or a reference sequence. The reference may be a genomic position and a start position of the expected sequence associated with the genomic position. The reference may be the genomic position and a reference sequence, e.g. a reference genome sequence as defined herein. Also, the reference need not be unique, i.e. the reference may link or point to more than one expected sequences, in particular to variants of an expected sequence.

Further, the nucleotide sequence data may be encoded in the FASTQ or the FASTA format. There are other formats like EMBL or GCG in which the nucleotide sequence data may be encoded as well.

Summarized, a method and system is proposed through which the probe information from the capture (hybridization) array or from beads may be used in the alignment procedure of sequencing reads. This may have the advantage that the alignment time can be reduced from around 1 hour to approximately 1 min. and may reduce the errors in alignment.

This may be important for enabling sequencing to become a routine application in the clinic. Apart from a gain in accuracy (which may be crucial in clinical applications), this could enable novel application of DNA sequencing in the clinic, such as analysis of resection margins during cancer surgery to see if sufficient material has been removed New workflows in the hospital may be enabled, as the time needed to complete the analysis of a sequencing run of a (cancerous) biopsy can be reduced to ≤5 h, which in its turn would enable one to give a patient the result of his or her biopsy the same day the biopsy has been taken. This may be an extremely significant improvement in clinical workflows.

The software labelling of a read with a reference of the expected sequence in the software output may be essential, should one wish to use the probe-information in the final (software) analysis. In particular, the labelling may be essential if one wants to be able to retain the probe information in the bio-informatics analysis to improve analysis speed and accuracy, as the software may have to know from which probe the sequenced fragment has come.

The software labelling may overcome the problem of locating the read on the right position in the genome, which may reduce the overall search time significantly, as this may now be done by a much faster comparison algorithm.

Software labelling the reads adds prior information to the read, the read becoming an object that may contain genomic position, expected sequence, location and quality information. This information may be used in look-up tables in the search process.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

TABLE 1

Reference Table - Figures/PatentIn Sequence Listing Protocol

| FIG. No. | Item (Reference No. in the Figure) | Nucleotide sequence, if more than one sequences shown in Figure | Correlated SEQ ID No. in PatentIn Sequence Listing |
|---|---|---|---|
| 7 | 78 | | 1 |
| 8 | 78 | | 1 |
| 9 | 80 | seq 1 | 2 |
|   | 80 | seq 2 | 3 |
|   | 80 | seq 3 | 4 |
|   | 80 | seq 4 | 1 |
| 10 | 80 | seq 1 | 2 |
|    | unnamed | seq 2 | 3 |
|    | unnamed | seq 3 | 4 |
|    | unnamed | seq 4 | 1 |
| 11 | unnamed | | 1 |
| 12 | 86 | seq 1 | 5 |
|    | 86 | seq 2 | 6 |
| 14 | 80 | | 1 |
| 15 | unnamed | seq 1 | 1 |
|    | unnamed | seq 2 | 1 |
|    | unnamed | seq 3 | 1 |
| 16 | 78 | | 1 |
| 17 | unnamed | seq 1 | 1 |
|    | unnamed | seq 2 | 1 |
|    | unnamed | seq 3 | 1 |
| 18 | 78 | | 7 |
| 19 | 80 | | 7 |
|    | 78 | | 7 |
| 20 | 90 | | 8 |
| 21 | 80 | seq 1 | 9 |
|    | unnamed | seq 2 | 10 |
| 22 | unnamed | | 10 |

Further embodiments of the present invention relate to:

1. A method for providing nucleotide sequence data (36), the method comprising the steps of:

Receiving basic nucleotide sequence data (30) comprising a determined sequence of identifiers for nucleotides (32) of a fragment of nucleic acids and comprising probe data (34) of a capture probe that has captured the fragment of nucleic acids;

Determining an expected sequence (38) of the fragment of nucleic acids by converting the probe data (34) into the expected sequence (38) with information interrelating the probe data (34) and the expected sequence (38);

Outputting the nucleotide sequence data (36) comprising the determined sequence of identifiers (32) and a reference to the expected sequence (38).

2. The method of embodiment 1, wherein the probe data (34) comprises position data (68, 70) and the expected sequence (38) is determined by interrelating the position data with the expected sequence.

3. The method of embodiment 1 or 2, wherein the reference to the expected sequence (38) comprises the expected sequence itself, a genomic position and/or a start position of the expected sequence within a reference sequence, and/or wherein the reference to the expected sequence (38) is also a reference for variants of the expected sequence (38).

4. The method of one of the preceding embodiments, wherein the expected sequence (38) is determined from a data table (42), the data table comprising records linking probe data and an associated expected sequence.

5. The method of one of the preceding embodiments, wherein the probe data (34) is converted by:

first converting the probe data into a genomic position (48) of the fragment of nucleic acids by reading the genomic position from a first data table (44), the first data table comprising records linking probe data with an associated genomic position; and second converting the genomic position (48) into the reference of the expected sequence by reading the reference from a second data table (46), the second data table comprising records linking a genomic position with an associated reference to an expected sequence.

6. The method of one of the preceding embodiments, wherein the expected sequence (38) comprises a sequence of identifiers for nucleotides;

wherein the expected sequence comprises information on variants of the sequence of identifiers.

7. The method of one of the preceding embodiments, further comprising the step of:

Aligning the determined sequence (32) to a reference nucleotide sequence by checking for an exact match of the expected sequence (38) with the determined sequence.

8. The method of embodiment 7, wherein the exact match is checked by string comparison of the determined sequence of identifiers (32) with the expected sequence of identifiers (38).

9. The method of embodiment 7 or 8, further comprising the step of:

Aligning the determined sequence (32) to a reference nucleotide sequence by performing a regular alignment algorithm, if no exact match is found for the expected sequence.

10. The method of one of the preceding embodiment, wherein the nucleotide sequence data is encoded in the FASTQ format, in the FASTA format, in the EMBL format or the GCG format.

11. A method for determining a sequence of nucleotides for a nucleic acid sample, the method comprising the steps of:

Providing a plurality of capture probes, each of the capture probes adapted to capture a specific sequence of a fragment of nucleic acids;

Hybridizing the capture probes with a plurality of fragments of nucleic acids generated by fragmenting a nucleic acid sample;

Sequencing the fragments of nucleic acids, thus generating for each fragment of nucleic acids a sequence of identifiers (32) for nucleotides;

Generating basic nucleotide sequence data (30) for each fragment of nucleic acids by associating the sequence of identifiers (32) of the fragment of nucleic acids with probe data (34) of the capture probe adapted to capture the fragment of nucleic acids;

Generating enriched nucleotide sequence data (36) for each fragment of nucleic acids by performing the method of one of the claims 1 to 10 on the basic nucleotide sequence data (30);

Aligning the enriched nucleotide sequence data (36) for each fragment of nucleic acids to an associated reference sequence.

12. A program element for providing nucleotide sequence data, which when being executed by a processor is adapted to carry out the steps of the method of one of the embodiments 1 to 11.

13. A computer-readable medium, in which a program element for providing nucleotide sequence data according to embodiment 11 is stored.

14. A sequencer device (10), wherein the sequencer device (10) is adapted to generate basic nucleotide sequence data (30) comprising a determined sequence of identifiers (32) for nucleotides of a fragment of nucleic acids and probe data (34) of a capture probe that has captured the fragment of nucleic acids;

wherein the sequencer device (10) is adapted to interrelate the probe data (34) with an expected sequence (38);

wherein the sequencer device (10) is adapted to generate nucleotide sequence data (36) comprising the determined sequence of identifiers (32) and a reference to the expected sequence (38).

15. The sequencer device (10) of embodiment 14, wherein the sequencer device (10) is adapted to perform the steps of one of the methods of embodiments 1 to 11.

The invention claimed is:

1. A method for determining a sequence of nucleotides for a nucleic acid sample, the method comprising the steps of:
providing a microarray including a plurality of sites, each site comprising a plurality of capture oligonucleotide probes, each of the capture oligonucleotide probes adapted to capture a specific sequence of a fragment of nucleic acids, each of the capture oligonucleotide probes being complementary in sequence to portions of a target nucleic acid, each of the capture oligonucleotide probes comprising two portions, said portions of the capture oligonucleotide probe being separated by a non-target complementary sequence label, the microarray comprising a chip encoding information or a label storing information for identifying a relationship between a respective one of the sites and reference sequences or an expected sequence associated with the capture oligonucleotide probes of that site;
fragmenting a nucleic acid sample into fragments of nucleic acids;
amplifying the fragments of nucleic acids by polymerase chain reaction (PCR), Rolling Circle Amplification (RCA) or Multiple Displacement Amplification (MDA);
thereafter, placing the fragments of nucleic acids in contact with the sites;
hybridizing the capture oligonucleotide probes with a plurality of the fragments of nucleic acids generated by fragmenting of the nucleic acid sample;
sequencing the fragments of nucleic acids, thus generating for each fragment of nucleic acids a sequence of identifiers for nucleotides;
reading the information from the microarray chip or label;
generating basic nucleotide sequence data for each fragment of nucleic acids by associating the sequence of identifiers of the fragment of nucleic acids with probe data of the capture oligonucleotide orobe adapted to capture the fragment of nucleic acids, the probe data including position data for the respective capture oligonucleotide probe, the expected sequence being determined from the information from the microarray chip or label by interrelating the position data with the expected sequence; and
generating enriched nucleotide sequence data for each fragment of nucleic acids based on the basic nucleotide sequence data, comprising:
identifying the sequence of the non-target complementary sequence label,
identifying the nucleotide sequence of the capture oligonucleotide probe adjacent to the non-target complementary sequence label, and
identifying the location of the sequence of the capture oligonucleotide probe on a reference genome, an expected sequence being defined by interrelating the information on said location on the reference genome with the corresponding sequence of the reference genome; and
outputting the nucleotide sequence data and a reference to the expected sequence, including providing a combination of (i) the determined sequence of identifiers of the nucleic acid target molecule and (ii) information on its location on the reference genome.

2. The method of claim 1, further comprising:
generating a table from the information read from the microarray, the table interrelating position data with the expected sequence.

3. In a sequencer device which includes a processor and which receives a microarray comprising a plurality of capture oligonucleotide probes, each of the capture oligonucleotide probes being complementary in sequence to portions of a target nucleic acid and comprising two portions, said portions of the capture oligonucleotide probe being separated by a non-target complementary sequence label, and optionally an immobilization moiety, each of the portions of the capture oligonucleotide probe adapted to capture a specific sequence of a fragment of nucleic acids, the microarray comprising a chip encoding information or a label storing information for determining a relationship between a site on the microarray and reference sequences or an expected sequence associated with the capture oligonucleotide probes in the site, a method for providing nucleotide sequence data, the method comprising:
hybridizing said capture oligonucleotide probe with a sample comprising a nucleic acid target molecule, wherein said target nucleic acid molecule comprises a sequence which is at least partially complementary to the capture oligonucleotide probe, the sequence of said capture oligonucleotide probe being at least partially complementary to the sequence of said fragment of nucleic acids, the sequence of said capture oligonucleotide probe being capable of capturing said fragment of nucleic acids by hybridization;
circularizing said nucleic acid target molecule by use of a polymerase activity;
amplifying said circularized nucleic acid target molecule;
reading the information encoded by the chip or stored in the label of the microarray;
with the processor, receiving basic nucleotide sequence data comprising a determined sequence of identifiers for nucleotides of a fragment of nucleic acids and probe data comprising position data of capture oligonucleotide probes in the microarray, the probe data including position data of the capture oligonucleotide probe that has captured the fragment of nucleic acids;
with the processor, determining an expected sequence of the fragment of nucleic acids by converting the probe data into the expected sequence with the information read from the microarray to interrelate the probe data and the expected sequence, the probe data including information on the location of the determined sequence of the nucleic acid target molecule on a reference genome obtained by a method for determining the sequence of a target nucleic acid molecule linked to genomic position information of said target nucleic acid molecule, wherein said sequence of the capture oligonucleotide probe is not the same as the expected sequence, comprising:
determining the sequence of the amplified nucleic acid target molecules by generating a sequence read of at least 2 nucleotides;
identifying the sequence of the non-target complementary sequence label;
identifying the nucleotide sequence of the capture oligonucleotide probe adjacent to the non-target complementary sequence label;
identifying the location of the sequence of the capture oligonucleotide probe on the reference genome, the expected sequence being defined by interrelating the information on said location on the reference genome with the corresponding sequence of the reference genome; and
outputting the nucleotide sequence data and a reference to the expected sequence, including providing a combination of (i) the determined sequence of identifiers of the nucleic acid target molecule and (ii) information on its location on the reference genome.

4. The method of claim 3, further comprising:
immobilizing said capture oligonucleotide probe-target nucleic acid complex on a solid phase.

5. The method of claim 4, further comprising:
removing non-bound nucleic acid molecules from the solid phase.

6. The method of claim 4, further comprising:
aligning the determined sequence to a reference sequence by checking for an exact match of the expected sequence with the reference sequence.

7. The method of claim 6, wherein the exact match is checked by string comparison of the determined sequence of identifiers with the expected sequence of identifiers.

8. The method of claim 6, further comprising the step of:
aligning the determined sequence to a reference nucleotide sequence by performing a regular alignment algorithm, if no exact match is found for the expected sequence.

9. The method of claim 3, wherein the reference to the expected sequence comprises the expected sequence itself, a genomic position and/or a start position of the expected sequence within a reference sequence, and/or
wherein the reference to the expected sequence is also a reference for variants of the expected sequence.

10. The method of claim 3, wherein the expected sequence is determined from a data table, the data table comprising records linking probe data and an associated expected sequence.

11. The method of claim 3, wherein the probe data is converted by:
first converting the probe data into a genomic position of the fragment of nucleic acids by reading the genomic position from a first data table, the first data table comprising records linking probe data with an associated genomic position; and
second converting the genomic position into the reference of the expected sequence by reading the reference from a second data table, the second data table comprising records linking a genomic position with an associated reference to an expected sequence.

12. The method of claim 3, wherein the nucleotide sequence data is encoded in the FASTQ format, in the FASTA format, in the EMBL format or the GCG format.

13. A sequencer device comprising:
a microarray comprising a plurality of capture oligonucleotide probes, each of the capture oligonucleotide probes being complementary in sequence to portions of a target nucleic acid molecule and comprising two portions, said portions of the capture oligonucleotide probe being separated by a non-target complementary sequence label, and optionally an immobilization moiety, each of the portions of the capture oligonucleotide probe being adapted to capture a specific sequence of a fragment of nucleic acids, the capture oligonucleotide probes hybridizing with fragments of nucleic acids in the nucleic acid sample, the basic nucleotide sequence data generated by circularizing said nucleic acid target molecule by use of a polymerase activity and amplifying said circularized nucleic acid target molecule, the microarray comprising a chip encoding information or a label storing information for identifying a relationship between a site on the microarray and reference sequences or an expected sequence associated with the capture oligonucleotide probes in the site;
a sequencing unit which reads the information encoded by the chip or stored in the label of the microarray and generates basic nucleotide sequence data, the sequencing unit receiving the microarray, the basic nucleotide sequence data comprising a determined sequence of identifiers for nucleotides of a fragment of nucleic acids and probe data, the probe data including position data of a respective capture oligonucleotide probe that has captured the fragment of nucleic acids;

a pre-processing unit which receives basic nucleotide sequence data from the sequencing unit and interrelates the probe data with an expected sequence using the information read from the microarray to generate enriched nucleotide sequence data, the enriched nucleotide sequence data comprising a determined sequence of identifiers and the expected sequence or a reference to the expected sequence;

an alignment unit which receives the enriched nucleotide sequence data and aligns the determined sequence of identifiers to a reference nucleotide sequence, including performing a string match comparison to see if the determined sequence matches the expected sequence and thereafter performing a regular alignment algorithm only if no exact match is found in the string match comparison;

wherein the sequence device generates nucleotide sequence data comprising the determined sequence of identifiers and a reference to the expected sequence.

* * * * *

```
                           SEQUENCE LISTING

<160> NUMBER OF SEQ ID NOS: 10

<210> SEQ ID NO 1
<211> LENGTH: 50
<212> TYPE: DNA
<213> ORGANISM: Homo sapiens
<220> FEATURE:
<221> NAME/KEY: exon
<222> LOCATION: (1)..(50)
<223> OTHER INFORMATION:
      ENSG00000142168|33031935|33032154|21_17|18

<400> SEQUENCE: 1
tgctgaaggg cgacggccca gtgcagggca tcatcaattt cgagcagaag          50

<210> SEQ ID NO 2
<211> LENGTH: 50
<212> TYPE: DNA
<213> ORGANISM: Homo sapiens
<220> FEATURE:
<221> NAME/KEY: exon
<222> LOCATION: (1)..(50)
<223> OTHER INFORMATION:
      ENSG00000142168|33031935|33032154|21_17|15

<400> SEQUENCE: 2
cgaaggccgt gtgcgtgctg aagggcgacg gcccagtgca gggcatcatc          50

<210> SEQ ID NO 3
<211> LENGTH: 50
<212> TYPE: DNA
<213> ORGANISM: Homo sapiens
<220> FEATURE:
<221> NAME/KEY: exon
<222> LOCATION: (1)..(50)
<223> OTHER INFORMATION:
      ENSG00000142168|33031935|33032154|21_17|16

<400> SEQUENCE: 3
gccgtgtgcg tgctgaaggg cgacggccca gtgcagggca tcatcaattt          50

<210> SEQ ID NO 4
<211> LENGTH: 50
<212> TYPE: DNA
<213> ORGANISM: Homo sapiens
<220> FEATURE:
<221> NAME/KEY: exon
<222> LOCATION: (1)..(50)
<223> OTHER INFORMATION:
      ENSG00000142168|33031935|33032154|21_17|17

<400> SEQUENCE: 4
gtgcgtgctg aagggcgacg gcccagtgca gggcatcatc aatttcgagc          50

<210> SEQ ID NO 5
<211> LENGTH: 220
<212> TYPE: DNA
<213> ORGANISM: Homo sapiens
<220> FEATURE:
<221> NAME/KEY: exon
<222> LOCATION: (1)..(220)
<223> OTHER INFORMATION: ENSG00000142168|33031935|33032154|21

<400> SEQUENCE: 5
```

```
gtttggggcc agagtgggcg aggcgcggag gtctggccta taaagtagtc gcggagacgg    60
ggtgctggtt tgcgtcgtag tctcctgcag cgtctggggt ttccgttgca gtcctcggaa   120
ccaggacctc ggcgtggcct agcgagttat ggcgacgaag gccgtgtgcg tgctgaaggg   180
cgacggccca gtgcagggca tcatcaattt cgagcagaag                         220
```

<210> SEQ ID NO 6
<211> LENGTH: 186
<212> TYPE: DNA
<213> ORGANISM: Homo sapiens
<220> FEATURE:
<221> NAME/KEY: exon
<222> LOCATION: (1)..(186)
<223> OTHER INFORMATION: ENSG00000196284|45345505|45345690|6

<400> SEQUENCE: 6

```
ccccccccat cgccccgtca cacagccgag tcacctttc cctttctaca ctccacactc    60
tcagtccccc accccgcccc tttccaagcg tgtcccgggc cgcagcagca gaaaccgcac   120
catctccacc cccacattct cctcgcggga agcgcagcag tgcctccaag ggttcttaaa   180
gcagag                                                              186
```

<210> SEQ ID NO 7
<211> LENGTH: 50
<212> TYPE: DNA
<213> ORGANISM: Homo sapiens
<220> FEATURE:
<221> NAME/KEY: exon
<222> LOCATION: (1)..(50)
<223> OTHER INFORMATION: ENSG00000196284|45345505|45345690|6_51

<400> SEQUENCE: 7

```
ctccacactc tcagtccccc accccgcccc tttccaagcg tgtcccgggc                50
```

<210> SEQ ID NO 8
<211> LENGTH: 801
<212> TYPE: DNA
<213> ORGANISM: Homo sapiens
<220> FEATURE:
<221> NAME/KEY: exon
<222> LOCATION: (1)..(801)
<223> OTHER INFORMATION: ENSG00000102468|47471072|47471885|13

<400> SEQUENCE: 8

```
agaaatcatt cacgagcccc tcaaagtcgc acaaaagaac tgcatgggaa agtaggaaga    60
gctgtctgca ccaagggact cctggttttcc acgggaatgg agtagctctc tgactgtctc   120
gttcatttca tcagacctcc ctctatgtgt atgtcataag ctgcaaggta gcaacagcca   180
ggagggcgga ccaaacaggc ttttttcttct ccctctttttt gctacatatt aatattggga   240
agttttcctt tgcttttgag agaaactgga gaaatggcct tttgtgcaga ttcccattaa    300
ggtaggtaag tggcactgtg gtaatttttt aggctgaagg gtgaagagag aacataaata   360
aggctagaaa acagtatgtc ctcggagtgc tgtgagtgtc yggcacttcc atccaaagcc   420
aacagtgttt gtgtccagag tggaattact gacattggcc acataggctc agggtggcta   480
ggcacgtctg tggtgataac tctgataaac tattagcact atttttattt aatagataca   540
ccattgaact ggcttatttt cttcagcaga aatatgccac ccagatatta ttcaaaacct   600
cacatgtggt aggaaataag ttggtttcgc agtaccaatt tttttccccc accagtaatg    660
acaacttgcc ttacttgtaa agaaagccct ttcccaagta ggtttctaaa ggaggcagtt   720
cgatctctct cttttttgcag gcatgaaaat atttttcctca atagttgggt tttgctacag   780
```

-continued

```
ttctatcacc ttctgttctt c                                            801

<210> SEQ ID NO 9
<211> LENGTH: 50
<212> TYPE: DNA
<213> ORGANISM: Homo sapiens
<220> FEATURE:
<221> NAME/KEY: exon
<222> LOCATION: (1)..(50)
<223> OTHER INFORMATION: ENSG00000102468|47471072|47471885|13c

<400> SEQUENCE: 9
acagtatgtc ctcggagtgc tgtgagtgtc cggcacttcc atccaaagcc             50

<210> SEQ ID NO 10
<211> LENGTH: 50
<212> TYPE: DNA
<213> ORGANISM: Homo sapiens
<220> FEATURE:
<221> NAME/KEY: exon
<222> LOCATION: (1)..(50)
<223> OTHER INFORMATION: ENSG00000102468|47471072|47471885|13t

<400> SEQUENCE: 10
acagtatgtc ctcggagtgc tgtgagtgtc tggcacttcc atccaaagcc             50
```